US008338114B1

(12) United States Patent
Goodwin

(10) Patent No.: US 8,338,114 B1
(45) Date of Patent: Dec. 25, 2012

(54) ENGINEERED HUMAN BRONCHO-EPITHELIAL TISSUE-LIKE ASSEMBLIES

(75) Inventor: Thomas J. Goodwin, Houston, TX (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 1111 days.

(21) Appl. No.: 11/789,117

(22) Filed: Apr. 19, 2007

(51) Int. Cl.

| | |
|---|---|
| ***C12Q 1/00*** | (2006.01) |
| ***C12Q 1/02*** | (2006.01) |
| ***C12Q 1/70*** | (2006.01) |
| ***C12N 5/07*** | (2010.01) |
| ***C12N 5/10*** | (2006.01) |

(52) U.S. Cl. ............... 435/7.21; 435/4; 435/29; 435/32; 435/325; 435/347; 435/383

(58) Field of Classification Search ............. 435/4, 7.21, 435/29, 32, 325, 347, 383
See application file for complete search history.

(56) References Cited

U.S. PATENT DOCUMENTS

| | | | | |
|---|---|---|---|---|
| 5,155,034 | A | 10/1992 | Wolf et al. | |
| 5,443,954 | A | 8/1995 | Reddel et al. | |
| 5,478,739 | A | 12/1995 | Slivka et al. | |
| 5,496,722 | A * | 3/1996 | Goodwin et al. | 435/371 |
| 5,516,680 | A | 5/1996 | Naughton et al. | |
| 6,117,674 | A | 9/2000 | Goodwin et al. | |
| 6,133,019 | A | 10/2000 | Herman | |
| 6,607,910 | B1 | 8/2003 | Dimitrijevich et al. | |
| 6,703,217 | B2 | 3/2004 | Herman et al. | |
| 2003/0054546 | A1 | 3/2003 | Petrecca et al. | |
| 2004/0023374 | A1 | 2/2004 | Rappaport et al. | |
| 2004/0175707 | A1 | 9/2004 | Hammond et al. | |
| 2004/0185558 | A1 | 9/2004 | Griguer et al. | |
| 2005/0255583 | A1 | 11/2005 | DePaola et al. | |
| 2006/0030043 | A1 | 2/2006 | Ma | |
| 2007/0161550 | A1 * | 7/2007 | Hancock et al. | 514/12 |

FOREIGN PATENT DOCUMENTS

| | | |
|---|---|---|
| WO | WO 00/54583 | 9/2000 |
| WO | WO 2005/056072 | 6/2005 |

OTHER PUBLICATIONS

Carterson et al. 2005. A549 Lung Epithelial Cells Grown as Three-Dimensional Aggregates: Alternative Tissue Culture Model for *Pseudomonas aeruginosa* Pathogenesis. Infection and Immunity, p. 1129-1140.*
Choe et al. 2006. Physiological 3D tissue model of the airway wall and mucosa. Nature Protocols. vol. 1, No. 1, p. 357-362.*
Dragomir et al. 2004. Increased chloride efflux in colchicine-resistant airway epithelial cell lines. Biochemical Pharmacology 68: p. 253-261.*
Catallo et al. Combustion Products of 1,3-Butadiene are Cytotoxic and Genotoxic to Human Bronchial Epithelial Cells. Environ Health Perspect 109:965-971 (2001).*
Becker et al. Respiratory syncytial virus infection of human primary nasal and bronchial epithelial cell cultures and bronchoalveolar macrophages. Am J Respir Cell Mol Biol. Apr. 1992;6(4):369-74; Abstract only p. 1-2.*
Becker et al. RSV infection of human airway epithelial cells causes moduction of the P-chemokine RANTES. American Journal of Physiology-Lung Cellular and Molecular Physiology. Volume: 272 Issue:3, p: L512-L520.*
Becker et al. RSV infection of human airway epithelial cells causes moduction of the P-chemokine Rantes. Am. J. Physiol. 272 (Lung CeZZ. Mol. Physiol. 16): L512-L520, 1997.*
Massin et al,, "Temperature Sensitivity on Growth and/or Replication of H1N1, H1N2 and H3N2 Influenza a Viruses Isolated from Pigs and Birds in Mammalian Cells" Veterinary Microbiology 142 (2010), pp. 232-241.
Hammond et al.. "Optimized Suspension Culture: The Rotating-Wall Vessel:" AM J Physiol renal Physiol 281 (2001), pp. F12-F25.
Nagase et al. "Expression and Function of Toll-Like Receptors in Eosinophils: Activation by Toil Like Receptor 7 Ligand" The Journal of Immunology (2003), pp. 3977-3982.

* cited by examiner

*Primary Examiner* — Taeyoon Kim
(74) *Attorney, Agent, or Firm* — Theodore U. Ro

(57) ABSTRACT

Three-dimensional human broncho-epithelial tissue-like assemblies (TLAs) are produced in a rotating wall vessel (RWV) with microcarriers by coculturing mesenchymal bronchial-tracheal cells (BTC) and bronchial epithelium cells (BEC). These TLAs display structural characteristics and express markers of in vivo respiratory epithelia. TLAs are useful for screening compounds active in lung tissues such as antiviral compounds, cystic fibrosis treatments, allergens, and cytotoxic compounds.

18 Claims, 9 Drawing Sheets
(2 of 9 Drawing Sheet(s) Filed in Color)

Course of Cellular Differentiation Into Tissues and Organs

ENGINEERED HUMAN BRONCHO-EPITHELIAL TISSUE-LIKE ASSEMBLIES

FEDERALLY SPONSORED RESEARCH STATEMENT

This work has been supported by NASA's Biological Sciences and Applications Division. The invention described herein is subject to the provisions of Section 305 of the National Aeronautics and Space Act of 1958, Public Law 85-568 (72 Stat. 435; 42 U.S.C. 2457).

PRIOR RELATED APPLICATIONS

Not applicable.

REFERENCE TO MICROFICHE APPENDIX

Not applicable.

FIELD OF THE INVENTION

In vitro three-dimensional (3D) human broncho-epithelial (HBE) tissue-like assemblies (3D HBE TLAs) from this point forward referred to as TLAs were engineered in Rotating Wall Vessel (RWV) technology to mimic the characteristics of in vivo tissues.

BACKGROUND OF THE INVENTION

Respiratory epithelium is critical in protecting humans from disease and acts as a barrier to invading microbes present in the air. Airway epithelial cells defend the host physiology by blocking paracellular permeability, modulating airway function through cellular interactions, and transporting inhaled microorganisms away via ciliated epithelial cells (Bals and Hiemstra, 2004, Cotran et al, 1999). Epithelial cells are regulators of the innate immune response and also induce potent immunomodulatory and inflammatory mediators (cytokines and chemokines), thus recruiting phagocytic and inflammatory cells and facilitating microbial destruction (Bals and Hiemstra, 2004; Knight and Holgate, 2003).

The respiratory epithelia defend the host through a complex multi-layered system of pseudo-stratified epithelial cells, a basement membrane, and underlying mesenchymal cells (Hiemstra and Bals, 2004). Ciliated, secretory, and basal epithelial cells are joined by intercellular junctions and anchored to the basement membrane via desmosomal interactions. Through tight junctions and the mucociliary layer, the basement membrane maintains polarity of the epithelium and presents a physical barrier between the mesenchymal layer and the airway (Knight and Holgate, 2003; Gibson and Perrimon, 2003). Spatial cellular relationships, cell membrane junctions, extracellular matrices (e.g., basement membrane and ground substances), and soluble signals (endocrine, autocrine, and paracrine) influence tissue differentiation. Complex recapitulated 3D models must emulate these complex cellular relationships to model characteristics of in situ airway epithelium.

Current models of in vivo lung epithelium are limited by fidelity of the model and scale. Traditional two-dimensional (2D) monolayer cultures such as immortalized human epithelial cell lines and primary normal human bronchial epithelial (NHBE) cells as well as air-liquid interface cultures (3D) fail to express the innate tissue fidelity characteristic of normal human respiratory epithelia (Carterson et al., 2005). Thus, their state of differentiation and intracellular signaling pathways differ from epithelial cells in vivo. Recently, 3D aggregates derived from an alveolar epithelial tumor cell line (A549) were used as targets for bacterial infection (Carterson et al., 2005). While superior to two dimensional cultures, the 3D aggregates lacked the functional and structural characteristics of airway epithelium in situ. Primary isolates of HBE cells provide a pseudo-differentiated model with structure and function similar to epithelial cells in vivo; however, this fidelity is short-lived in vitro (Gray et al, 1996). Air-liquid interface cultures of primary HBE cells (or submerged cultures of human adenoid epithelial cells Wright et al, 2005) are grown on collagen-coated filters in wells, on top of a permeable filter. These cells receive nutrients basolaterally and their apical side is exposed to humidified air. The result is a culture of well-differentiated heterogeneous (ciliated, secretory, basal) epithelial cells essentially identical to airway epithelium in situ (Adler and Li, 2001). Although this model mimics the fidelity of the human respiratory epithelium in structure and function, maintenance of consistent cultures is difficult, time consuming, and restricted to small-scale production.

Culturing normal 3D epithelium configurations larger than 3 mm is problematic using traditional in vitro culture technology. Short-term cultures have been accomplished but, long-term growth requires sophisticated, defined culture media or in vitro transformation to increase longevity. To address this, horizontally rotating cylindrical tissue culture vessels or rotating wall vessels (RWV) developed at NASA's Johnson Space Center (Schwarz et al, U.S. Pat. No. 5,026,650) have been used to model many 3D tissues (Goodwin et al, 1988, 1992, and 1993) (Table 1). This technology allows the recapitulated tissues to be used as host targets for viral infectivity (Goodwin et al., 2000) by providing controlled supplies of oxygen and nutrients, with minimal turbulence and extremely low shear (Schwarz et al, 1992). These vessels rotate the wall and culture media inside at identical angular velocity, thus continuously randomizing the gravity vector and holding particles such as microcarriers and cells relatively motionless in a quiescent fluid (Schwarz et al 1992; Tsao et al, 1992).

TABLE 1

3D TISSUES ENGINEERED IN THE ROTATING WALL VESSEL

| NORMAL | Ref |
|---|---|
| Bovine Cartilage (chondrocytes) | (Baker, 1997) |
| Rat Cardiomyocytes | (Bursac, 2003) |
| Human Bone (Osteoblast) | (Klement, 2004; Wang, 2005) |
| Human Cornea | (O'Connor, 1999) |
| Human Kidney | (Goodwin, 1993; Hammond, 1997) |
| Human Liver | (Yoffe, 1999) |
| Human Lymphoid | (Margolis, 1997; Pellis, 1997) |
| Human Neural Progenitor | (Goodwin, 2003; Goodwin, 2005) |
| Human Renal Proximal Tubule | (Hammond, 1997) |
| Human Small Intestinal Epithelial | (Goodwin, 1993) |
| CANCER | |
| Human Colon | (Goodwin, 1988; Goodwin, 1992) |
| Human Lung | (Vertrees, 2005) |
| Human Ovarian | (Goodwin, 1997) |
| Human Prostate | (Wang, 2005) |

Optimally, a cell-based respiratory epithelia model would reproduce the structural organization, multicellular complexity, differentiation state, and function of the human respiratory epithelium. Here we report the successful engineering of the first in vitro model of the human respiratory epithelium using primary mesenchymal hBTCs as the foundation matrix and an adult HBE immortalized cell line BEAS-2B as the overlying component. The RWV culture system provides ease of manipulation, consistency in culture conditions, and well-differentiated TLAs that share structural and functional characteristics of the human respiratory epithelium. When combined with a solid matrix, cocultivation of epithelial and mesenchymal cells in RWVs allow cells to auto assemble into 3D tissue-like masses that we postulate fulfill four of the five basic stages of tissue regeneration and differentiation (FIG. 2). Like the air-liquid interface model (O'Brien et al, 2002), the epithelial cell organization of the TLAs improves the expression of airway epithelial characteristics, and also cellular communication. Thus, TLAs represent a physiologically relevant model of the human respiratory epithelia that can be used in large-scale production for prolonged periods.

TABLE 2

ABBREVIATIONS

| Abbr | Term |
|---|---|
| 2D | Two-Dimensional |
| 3D | Three-Dimensional |
| ATCC ® | American Tissue-type Culture Collection |
| BE | Broncho-Epithelial |
| BME | Eagle's Basal Medium |
| BSA | Bovine Serum Albumin |
| BTC | Broncho-Tracheal Cells |
| BV | Budding Virus |
| CF | Cystic Fibrosis |
| CMF-PBS | calcium- and magnesium-free PBS |
| DEAE | Diethylamino Ethanol |
| DMEM | Dulbecco's MEM |
| DPBS | Dulbecco's PBS |
| ECM | Extracellular Matrix |
| EMA | Epithelial Membrane Antigen |
| EMEM | Eagle's MEM |
| FBS | Fetal Bovine Serum |
| FVIII | Factor VIII |
| GTSF | Glucose Trisugar Formula |
| H&E | Haematoxylin and Eosin |
| hBE | Human Broncho-eptihelial |
| hBTC | Human Mesenchymal BTC |
| HIV | Human Immunodeficiency Virus |
| ICAM | Intercellular Adhesion Molecule |
| IHC | Immunocytochemistry |
| IMDM | Iscove's Modified Dulbecco's Medium |
| MEM | Minimal Essential Medium |
| MOI | Multiplicity of Infection |
| MV | Microvilli |
| NHBE | Primary Normal hBE |
| PBS | Phosphate-Buffered Saline |
| PECAM | Platelet/Endothelial Cell Adhesion Molecule |
| pfu | Particle Forming Units |
| pi | Post Infection |
| PIV | Parainfluenza Virus |
| RARβ | Retinoic Acid Receptor beta |
| RSV | Respiratory Syncytial Virus |
| RWV | Rotating Wall Vessel |
| SEM | Scanning Electron Micrograph |
| SPA | Surfactant Protein A |
| SPG | Sucrose-Phosphate-Glyoxylic acid |
| TEM | Transmission Electron Micrograph |
| TJ | Tight Junction |
| TLA | Tissue-Like Assemblies (3D-HBE) |
| V | Vacuole |
| VNC | Virus Nucleocapsid |
| wt | Wild-Type |
| ZO | Zonula Occludens |

SUMMARY OF THE INVENTION

The construction of a functionally accurate, large-scale, 3D in vitro tissue model of the human airway is a major advance for lung research. The recapitulation of large TLAs that express differentiated epithelial and mesenchymal cell markers offers a multitude of possibilities for cell biological investigations. Functional epithelial cell brush borders with extracellular matrix and basal lamina components represent ordering of tissue and cellular polarity nurtured by the molecular conditions and physical orientations of the culture system. These data are confirmed in FIG. 4 (NC) and FIG. 5 (TEMs) and represent concomitant cellular differentiation marker expression and architectural ordering when compared to normal human tissue. Additionally, this 3D model demonstrates a significantly diminished requirement for complex culture media in the RWV culture system. The growth of mesenchymal and epithelial cells in the absence of complex media infers specific cell-cell interactions and the production of the paracrine and autocrine factors essential to the growth, development and differentiation of these fragile tissues.

This model of human TLAs embodies many aspects of differentiation observed in other in vitro and in vivo cell and organ models. Primary distinctions for this model are: (i) the overall scale of the model, (ii) the ability to culture epithelium for periods in excess of 40 days without loss of functional cell markers, (iii) the ability to maintain viral production and cellular repair while maintaining the model, and (iv) the ability of the system to respond to extensive analyses and manipulations without the termination of a given experiment. Future experiments will use genomic and proteomics technologies to clarify and characterize the potential of this new model system. Of particular interest will be regulation of unique cytoskeletal proteins such as villin, functional markers such as tubulin, ZO-1, EMA, ICAM-1, a myriad of inflammatory response modifiers, and other markers that may be represented more accurately by large-scale 3D modeling.

The molecular basis of inflammatory responses and pathogenesis of the human lung to many airborne and blood borne infections may be investigated with the advent of this new technology. Further, clinical response and treatment of diseases may be accomplished more efficiently as a result of rapid vaccine development (Deatly et al, submitted). Analogous to the data presented for RSV and PIV, the human immunodeficiency virus (HIV) can replicate in human 3D lymphoid tissues and complex epithelium maintained in the RWV, thus immunodeficiency virus-host interactions in the RWV culture system may be possible (Moyer et al, 1990, 1990b, Margolis 1997). Therefore broad application of this culture model may lead to advances in understanding the developing human lung, the potential treatment of a myriad of clinical conditions, and advances in regenerative medicine.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 4W, and FIG. 4Y) and recapitulated TLAs (FIG. 4B, FIG. 4D, FIG. 4F, FIG. 4H, FIG. 4J, FIG. 4L, FIG. 4N, FIG. 4P, FIG. 4R, FIG. 4T, FIG. 4V, FIG. 4X, and FIG. 4Z) formed in the RWV. Photos are arrayed in matched pairs showing the normal human tissue and the TLAs were stained for PECAM-1 (FIG. 4A and FIG. 4B), EMA (FIG. 4C and FIG. 4D), tubulin (FIG. 4E and FIG. 4F), cytokeratin 8 (FIG. 4G and FIG. 4H), Factor VIII (FIG. 4I and FIG. 4J), mucin (FIG. 4K and FIG. 4L), villin (FIG. 4M and FIG. 4N), cytokeratin 18 (FIG. 4O and FIG. 4P), ZO-1 (FIG. 4Q and FIG. 4R), ICAM-1 (FIG. 4S and FIG. 4T), and collagen IV (FIG. 4Y and FIG. 4Z). Sample pairs FIG. 4U and FIG. 4V and FIG. 4W and FIG. 4X are H&E histologies demonstrating human tissue organization and TLA cell density. All samples are shown at 400× magnification.

FIG. 5A and FIG. 5B (mag. ×7,500) show TLAs that are multilayered (6 or 7 layers of long thin cells with dark nuclei) and demonstrate extracellular matrix material between the cells; FIG. 5C and FIG. 5D (mag. ×7,500) demonstrate both mesenchymal and epithelial cells (oval and elongated nuclei) lying close to the bead surface; FIG. 5E and FIG. 5F (mag ×50,000) demonstrate cellular tight junctions (TJ) and microvilli (MV) are visible in FIG. 5F.

FIG. 6A and FIG. 6B demonstrate healthy non-infected (smooth) epithelium; FIG. 6C and FIG. 6D demonstrate clusters of budding virus (BV) atop the epithelium on day 2 and 4 post infection (pi); FIG. 6E illustrates the result of viral infection of the epithelial layer on day 8 pi. Notice the pock-marked appearance of the once smooth epithelium. FIG. 6F demonstrates an inset of budding virus masses from an infected epithelium on day 12 pi.

FIG. 7A is an uninfected micrograph showing a tight junction (TJ) between cells at time zero. FIG. 7B demonstrates viral nucleocapsids (VNC) present in the perinuclear area of the cell at 1 hr pi. Both FIG. 7A and FIG. 7B shown at mag. ×50,000. FIG. 7C (mag. ×50,000) and FIG. 7D (mag. ×12,000) illustrate the presence of budding virus (BV) at 2 and 4 days pi, respectively, and vacuoles (Vs) in FIG. 7D at day 4 pi. FIG. 7E (mag. ×50,000) and FIG. 7F (mag. ×25,000) show VNC present in the cells at days 8 and 12 pi, respectively.

DETAILED DESCRIPTION OF THE INVENTION

Figure 1:
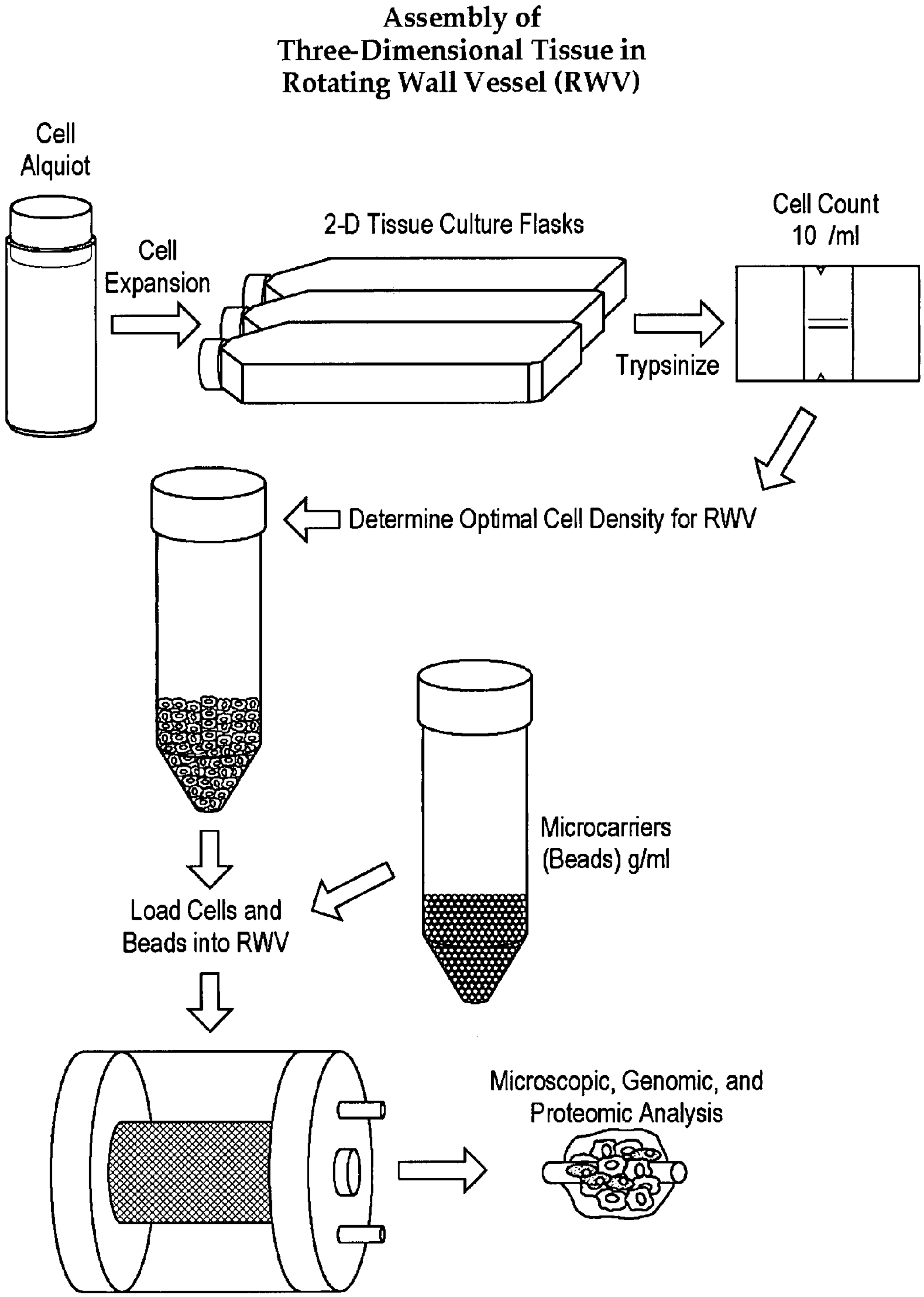
FIG. 1: Tissue assembly process in a Rotating Wall Vessel.
Figure 2:
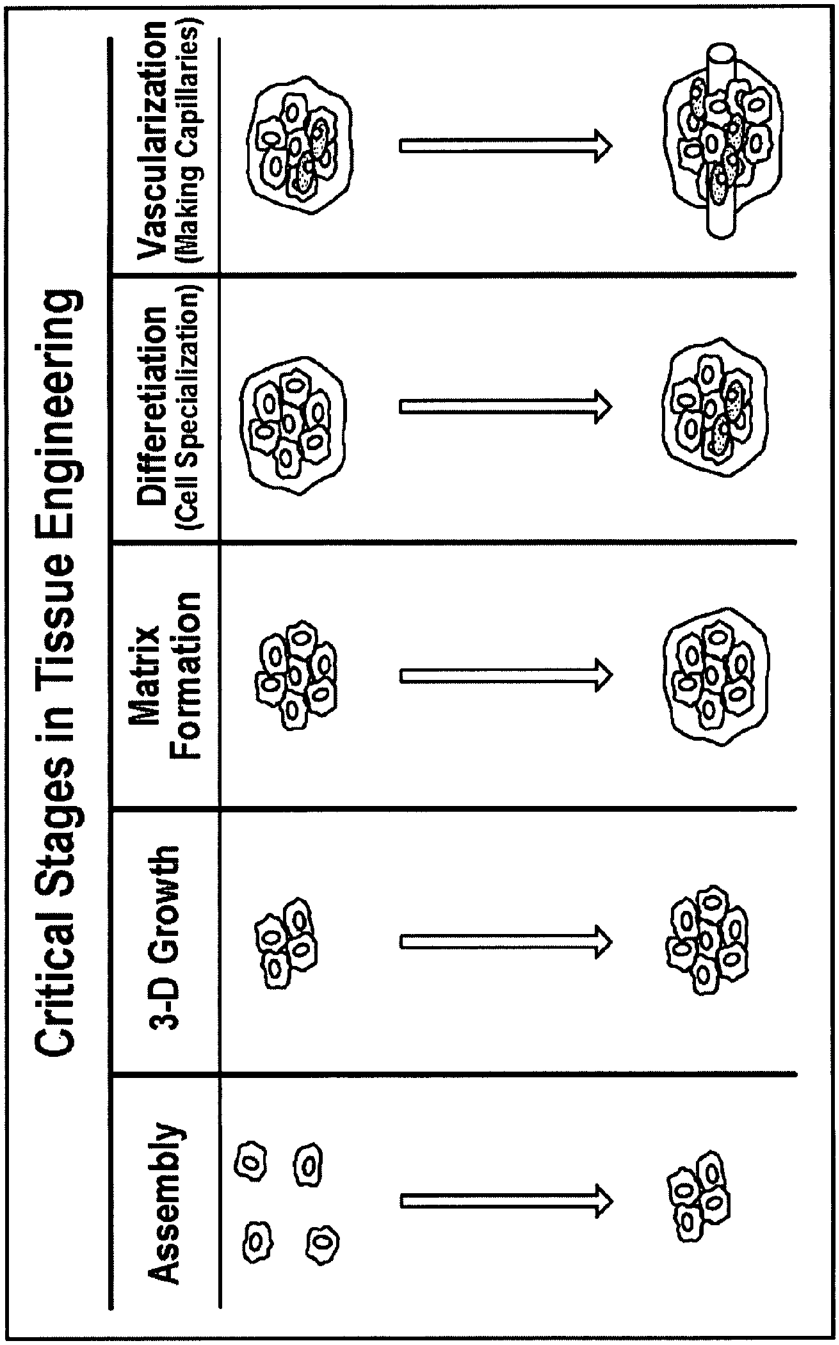
FIG. 2: Five stages of tissue development and assembly.

In vitro TLAs were engineered in RWV to mimic the characteristics of in vivo tissues thus providing a tool to study human respiratory viruses and host cell interactions. The TLAs were bioengineered onto collagen-coated cyclodextran microcarriers using primary human mesenchymal bronchial-tracheal cells (HBTC) as the foundation matrix and an adult human bronchial epithelial immortalized cell line (BEAS-2B) as the overlying component. The resulting TLAs share significant characteristics with in vivo human respiratory epithelium including polarization, tight junctions, desmosomes, and microvilli. The presence of tissue-like differentiation markers including villin, keratins, and specific lung epithelium markers, as well as the production of tissue mucin, further confirm these TLAs differentiated into tissues functionally similar to in vivo tissues. Increasing virus titers for human respiratory syncytial virus (wtRSVA2) and parainfluenza virus type 3 (wtPIV3 JS) and the detection of membrane bound glycoproteins over time confirm productive infections with both viruses. Therefore, TLAs mimic aspects of the human respiratory epithelium and provide a unique capability to study the interactions of respiratory viruses and their primary target tissue independent of the host's immune system.

TLAs are produced in cell cocultures with mesenchymal bronchial-tracheal cells (BTC) and bronchial epithelium cells (BEC). These TLAs express markers of in vivo respiratory epithelia and display structural characteristics of in vivo respiratory epithelia. In one embodiment of the invention primary human mesenchymal bronchial-tracheal cells (hBTC) and human bronchial epithelial immortalized cells (BEAS-B2) are cocultured.

TLAs can be produced in a RWV with culture media and microcarriers by inoculating with BTC cells, growing BTC cells for 24 to 240 hours, and subsequently inoculating with BEC cells. The coculture can be grown for 24 to 960 hours to produce TLAs. These TLAs express markers of in vivo respiratory epithelia and display structural characteristics of in vivo respiratory epithelia.

The microcarriers and culture media can be selected to have less than a 10% difference in density, more preferably less than a 5% difference in density, and most preferably less than a 2% difference in density. The difference in density can be calculated as 100 times the fraction of microcarrier density over media density or media density over microcarrier density. Acceptable differences in density range continuously from 90%-110% including all intermediate values.

Compounds can be assayed using TLAs to determine antiviral activity, identify putative CF treatments, quantitate allergen activity, or determine compound cytotoxicity. One assay may be performed by dividing TLA producing cocultures into two or more separate cocultures. One set of experimental TLAs can be exposed to a test compound, while a second set of control TLAs are not. Additional control TLAs may be exposed to compounds with a known activity. TLAs can be assayed in the presence or absence of viral infection, with cell lines from cystic fibrosis sufferers, as well as other lung diseases.

Mesenchymal bronchial-tracheal cells (hBTC) include primary cultures of mesenchymal bronchial-tracheal cells, as well as fibroblasts and myofibroblasts. Bronchial cell strains include HFL1, HS-1Lu, CCD-8Lu, CCD-13Lu, CCD-25Lu; human embryonic pulmonary fibroblast (W138); and fetal lung fibroblasts (IMR-90, MRC-5, HFLF). Cell lines may be from a variety of sources including mammals, primates (DBS-FCL-1), dog, cat (FC2.Lu), mouse, and rat (RLF). Cell lines may or may not be transformed with a virus prior to or after inoculation. Some cell lines that contain virus include WI-38-VA13, WI-26-VA4, XP12RO, HFL-1, and M3E3/C3.

Bronchial epithelial cell lines include primary cultures of bronchial epithelial cells (BEC), normal bronchial epithelium (e.g. 16-HBE, HBE135, NHBE, HTBE); immortalized bronchial epithelium (BEAS-2B, BEAS-S6, BEAS39, BEP2D, BES-1A1, BET-1A, BZR, HEp-2, NL20, SK-LU 1); fetal broncho epithelium (9HTEo-); fetal lung epithelium (MRC-5); alveolar epithelium (R3/1, L2); trachea epithelium (CF-PEo); and Cystic Fibrosis (CF) epithelium (CFSMEo, CFBE41o-, IB3-1). Cell lines may be from a variety of sources including mammals, primates (4 MBr-5, 12 MBr6), dog, cat (AK-D), mouse (MM14.Lu), and rat (E1A-T2). Cell lines may or may not be transformed with a virus prior to or after inoculation. Some cell lines that contain viruses include HBE135-E6E7, HBE4-E6/E7, HBE4-E6/E7-C1, and BBM.

Other lung and bronchial cell lines (e.g. FHs-738Lu, HE-LU(Rifkin), Hs-412.Lu, Hs-115.Lu) and numerous carcinogenic cell lines (e.g. A549, NCI-H441, 16HBE4o-, NCI-H292) are also available for cell culture using the RWV. Although these cell lines are in various stages of characterization, they may prove useful as either mesenchymal or epithelial cell lines depending upon their ability to differentiate in the RWV under various growth conditions. AMERICAN Type Culture Collection™ (ATCC®) (Manassas, Va.), has many publicly available cell strains, incorporated herein by reference.

Respiratory Syncytial Virus (RSV) is available from a variety of sources. Examples include human respiratory syncytial virus A-2 (ATCC VR-1540™), human respiratory syncytial virus B (ATCC VR-1400™), human respiratory syncytial virus 9320 (ATCC VR-955™), human respiratory syncytial virus Wash/18537/'62 (ATCC VR-1580™), human respiratory syncytial virus Long (VR-26), among others.

Parainfluenza virus (KV) includes parainfluenza virus 1 (ATCC VR-94™), parainfluenza 2 (ATCC VR-92™), parainfluenza Greer (ATCC VR-1381™), Parainfluenza 4a (ATCC VR-1378™), parainfluenza 4b (ATCC VR-1377™), and parainfluenza 5 DA (ATCC VR-263™).

Other viruses that infect the naso-pharynx, trachea, and lungs include human rhinoviruses (HRV), coxsackieviruses, echoviruses, severe acute respiratory syndrome virus (SARS), adenovirus, influenza A and B, Hantavirus, and cytomegalovirus (CMV). Some viruses have multiple symptoms that could include lung infection. Some common viruses associated with multisystem syndromes include paramyxovirus species (measles), varicella-zoster virus, Epstein-Barr virus, CMV, herpes simplex virus, and human immunodeficiency virus (HIV).

GTSF-2 is a unique trisugar-based medium, containing glucose, galactose, and fructose formulated at NASA's Johnson Space Center (U.S. Pat. No. 5,846,807). GTSF-2 media can be used with or without supplemental ingredients including 10% fetal bovine serum (FBS). Although GTSF-2 is optimized for RWV cultures, other culture media may be substituted and function in a similar manner. Culture media include commercial media supplied by ATCC® (Manassas, Va.), Sigma-Aldrich® (St. Louis, Mo., U.S.A.), GibCo® (Invitrogen®, Carlsbad, Calif.), EuroClone® (Milano, Italy) and others. Common tissue culture media include Eagle's Basal Medium (BME), Dulbecco's Modified Eagle's Medium (DMEM), DMEM: F12 Medium, Eagle's Minimum Essential Medium (EMEM), F-12K Medium, Iscove's Modified Dulbecco's Medium (IMDM), Leibovitz's L-15 Medium, McCoy's 5A Medium Modified, RPMI 1640 Medium, or customized culture media with various salts, amino acids, peptides, and supplements that facilitate cell growth.

Microcarriers are available in a variety of materials including Cylindrical DEAE cellulose anion exchangers (e.g. DE-52, DE-53), DEAE-Sephadex™ A-50, polystyrene, derivatized polyacrylamide, cross-linked dextran, DEAE-dextran, silicone, gelatin, glass, or other suitable material. Changes in porosity and charge can affect cell growth on various microcarriers. Microcarriers can be coated with various surface compounds to improve cell growth including collagen, pronectin, modified collagen, denatured collagen, DEAE, peptides, and charged compounds. One example is collagen-coated cyclodextran microcarriers where the dextran beads are coated with cross-linked denatured collagen and provide a natural surface for cell growth. Microcarriers are available from various sources examples include glass-coated microcarriers (Biosil®, Paterson, N.J.), Ventregel® collagen microcarriers (Ventrex® LAB., Portland, Me.), CultiSpher™ G gelatin microcarriers (Sigma®, St. Louis, Mo.), Gelibead™ cross-linked gelatin microcarriers (KC-Biologicals™, Lenexa, Kans.), collagen-coated polystyrene (Kontes Life Sciences Products®, Vineland, N.J.), Cytodex-1™ DEAE-dextran microcarriers (Pharmacia® Piscataway, N.J.) and Cytodex-3™ collagen-linked DEAE-dextran microcarriers (Pharmacia® Piscataway, N.J.).

Rotating Wall Vessel (RWV) is a horizontally rotated culture vessel with zero headspace and center oxygenation. The RWV is a suspension culture vessel optimized to produce laminar flow and minimize the mechanical stresses on cell aggregates in culture. In an embodiment, the RWV provides an environment for enhancing the culture of cells and living 3-dimensional tissues by controlling the fluid mechanical environment to achieve the predetermined culture characteristics. More specifically, use of the RWV effectuates the capability to simultaneously achieve a culture environment with reduced fluid shear stress, freedom for 3-dimensional spatial orientation (of suspended particles), and localization of particles with differing (or similar) sedimentation properties in a similar spatial region (collocation). The minimal fluid shear stress obtainable in unit gravity (i.e., 9.8 $m/sec^2$) is determined by the gravitationally induced motion of the suspended particles of the horizontally rotating culture vessel through the culture medium. Further, the RWV provides a means for a supply of nutrients and removal of metabolic waste products. This is accomplished either by perfusion of media through an external media perfusion loop, direct injection to the culture media, or exchange of these molecules across a diffusion membrane. Additional details are found in U.S. Pat. No. 5,155,034 to Wolf et al., which is incorporated by reference in its entirety. Terminal velocity in a RWV culture is minimized by choosing microcarrier beads and culture media as close in density as possible. Preferably the microcarrier beads and culture media will have less than a 10%, 9%, 8%, 7%, 6%, 5%, 4%, 3%, 2%, or 1% difference in density. Most preferably the microcarrier beads and culture media would have equivalent densities with less than 1% difference in density.

TLAs are engineered cells comprising epithelial and mesenchymal cell types. TLAs share significant characteristics with in vivo human respiratory epithelium including polarization, tight junctions, desmosomes, microvilli, and tissue-like differentiation markers.

Tissue-like differentiation markers include: basement membrane and extracellular matrix components (e.g., collagen IV); epithelial and mesenchymal cell markers; specific lung epithelium markers; cell adhesion molecules; extracellular matrix (ECM) markers; surfactant proteins; secretory proteins; inflammatory response modifiers; tight junctions (including ZO-1); polarization (e.g. EMA); claudins; collagens; collagen IV; cytokeratins; cytokeratin 8; cytokeratin 18; epithelial membrane antigen (EMA); epithelial cell surface marker (EPM-1), Factor VIII; intercellular adhesion molecule (ICAM-1); keratins; laminin, lectin; lysozyme, mucin; platelet/endothelial cell adhesion molecule (PECAM-1); retinoic acid receptor beta (RARβ); surfactant protein A (SPA); tubulin; villin; vimentin; and zonula occludens-1 (ZO-1), among other differentiation specific markers.

Phenotypic or qualitative traits include cell shape, cell types, cell anomalies, TLA structure, and other morphological characteristics. Examples include traits such as the presence and/or position of cell differentiation markers in the TLA.

Quantitative traits include cell size measurements, fluorescence, IHC measurement, and other analytical measurements. Examples include the measurement of cell differentiation markers in the TLA.

Example 1

Materials & Methods

Viruses and strains used in certain embodiments of the invention are set forth in Table 3.

TABLE 3

| VIRUSES & STRAINS | | |
|---|---|---|
| Virus | Genotype | Ref |
| wtRSVA2 | wild-type human respiratory syncytial virus | ATCC VR-1540 ™ |
| wtPIV3 JS | wild-type parainfluenza virus type 3 | ATCC VR-94 ™ |
| Strain | Description | Ref |
| hBTC | primary human mesenchymal bronchial-tracheal cells | CAMBREX |
| BEAS-2B | human bronchial epithelial immortalized cell line | ATCC CRL-9609 ™ |
| HEp-2 | HeLa contaminant | ATCC CCL-23 ™ |
| LLC-MK2 | Kidney | ATCC CCL-7 ™ |

Cell Cultures and Media

Mesenchymal cells (hBTC) from human bronchi and tracheae were obtained from the lung mucosa of multiple tissue donors through Cambrex Biosciences® (Walkersville, Md.). BEAS-2B epithelial cells were obtained from ATCC® (Manassas, Va.). All were harvested and banked at the NASA Johnson Space Center's Laboratory for Disease Modeling and shown to be free of viral contamination by survey of a panel of standard adventitious viruses (e.g. HIV, hepatitis, herpes) conducted by the manufacturer. Cells were initiated as monolayers in human fibronectin coated flasks (BD Biosciences®, San Jose, Calif.) and propagated in GTSF-2 media supplemented with 10% FBS. All cell cultures were grown in a FORMA® (Marietta, Ohio) humidified $CO_2$ incubator with 95% air and 5% $CO_2$, and constant atmosphere at a temperature of 37° C. Normal hBTC mesenchymal and BEAS-2B human lung cells were passaged as required by enzymatic dissociation with a solution of 0.1% trypsin and 0.1% EDTA for 15 minutes at 37° C. After incubation with the appropriate enzymes, the cells were centrifuged at 800 g for 10 minutes in Corning conical 50 ml centrifuge tubes. The cells were then suspended in fresh medium and diluted into T-flasks with 30 ml of fresh growth medium. BEAS-2B epithelial cells were passaged as required by dilution at a 1:4 ratio with GTSF-2 media in T-flasks.

RWV Cultures

Normal mesenchymal cell monolayers were removed from T-75 flasks by enzymatic digestion, washed once with CMF-PBS, and assayed for viability by trypan blue dye exclusion (Invitrogen®, Carlsbad, Calif.). Cells were held on ice in fresh growth medium until inoculation. The primary inoculum for each coculture experiment was $2\times10^5$ hBTC mesenchymal cells/ml in a 55-ml RWV with 5 mg/ml of Cytodex-3™ microcarriers 120 μm in diameter. Cultures were allowed to grow for a minimum of 24 to 48 hours before the medium was changed. Thereafter, fresh medium was replenished by 65% of the total vessel volume each 20 to 24 hours. BEAS-2B epithelial cells were added at $2\times10^5$ cells/ml on day 4. As metabolic requirements increased, fresh medium was supplemented with an additional 100 mg/dl of glucose. Coculture experiments in the RWV were grown in GTSF-2 supplemented with 10% fetal bovine serum (Goodwin et al 1992, 1993). The optimal period of culture was 15-20 days prior to infection with virus. Experiments were cultured for up to 40 days total including post infection (pi). Viable cocultures grown in the RWV were harvested over periods up to 21 days and prepared for various viral infectivity assays. All RWV cell cultures were grown in a Forma® (Marietta, Ohio) humidified $CO_2$ incubator with 94.5% air and 5.5% $CO_2$ providing constant atmosphere and a temperature of 35.5° C. to mimic that of the nasopharyngeal epithelium (McFadden, 1985).

3D Cell Growth Kinetics

The cocultures were sampled over the course of the experiments, generally at 48-hour time points, in order to establish a cellular development profile. The parameters of glucose utilization and pH were surveyed via i-STAT® (Princeton, N.J.) clinical blood gas analyzer to determine the relative progress and health of the cultures and the rate of cellular growth and viability.

Immunocytochemistry (IHC)

Normal human lung tissue samples and TLA tissue sections designated for histological and immunohistological staining were washed three times with gentle agitation in CMF-PBS for 5 minutes to remove foreign protein residues contributed by the media. The TLAs were then transferred to 50 ml polystyrene tubes and covered with 10% buffered formalin in PBS (#15740, Electron Microscopy Science (EMS) ™, Hatfield, Pa.) overnight at 4° C. and washed three times in PBS. TLAs were centrifuged at low speed (1000×g) to concentrate the bead-cell assembly. Warm noble agar (1 ml) was added for additional stabilization. TLAs were embedded in paraffin-blocks by standard methods, and light sections cut at 3-5 um on a MICRON® HM315 microtome (Walldorf, Germany). All unstained sections were stored at 20° until stained with haematoxylin and eosin (H&E) or with a panel of differential and developmental membrane receptor antibodies. The sections were deparaffinized by normal procedure (Goodwin, 1988), antigen retrieved by protease or citrate, and blocked with a normal rabbit or mouse sera –0.5% Tween® 20 blocking solution. The primary antibody (as identified in Table 4) diluted in the blocking solution was incubated on sections between 9 and 30 minutes as required, rinsed with distilled water, and incubated with anti-mouse, -goat, or -rabbit-antibodies conjugated with horseradish peroxidase. The second antibody (Dako EnVision System™) was applied using an automated immunohistochemical stainer (Dako®, Carpinteria, Calif.). Slides were examined under a Zeiss® Axioskop™ (Hamburg, Germany) microscope and images captured with a Kodak® DC290 Zoom (Rochester, N.Y., USA) digital camera.

TABLE 4

| HUMAN IMMUNOHISTOCHEMISTRY ANTIBODIES | | |
|---|---|---|
| Antibody | Manufacture | Dilution |
| Rabbit anti- ZO-1 | Zymed, #61-7300 | 1:3000 |
| Mouse anti-Human Villin | Neomarkers, Ezrin p81/80K Cytovillin Ab-1, Clone 3C12 | 1:40 |
| Mouse anti-Human EMA | Dako, #N1504, Clone E29 | 1:1500 |
| Mouse anti-Human Endothelial Cell Membrane PECAM-1 (CD 31) | Dako, #N1596, Clone JC70A | 1:500 |
| Mucin Stain Kit | Ventana Medical Systems | NA |
| Mouse anti-Human Cytokeratin 8 | Dako, #M0888, Clone RCK 108 | predilute |
| Mouse anti-Human Laminin | Dako, #M0638, Clone 4C7 | 1:1000 |
| Mouse anti-Swine Vimentin | Dako, #M0725, Clone V9 | 1:2000 |
| Mouse anti-Human Cytokeratin 18 | Dako, #N1589, Clone LP34, 34 beta E12 | predilute |
| Rabbit anti-Human Von Willebrand Factor | Dako, #N1505 | 1:75 |
| Fibronectin | Dako | 1:500 |
| Tubulin | ProMega Cat. No. #946, clone 5G8 | 1:1000 |
| Collagen IV | Dako #N1536 clone CIV 22 | predilute |

Transmission Electron Microscopy (TEM)

TLA TEM samples were washed three times with 0.1 M sodium cacodylate buffer pH 7.4 (#11652, Electron Microscopy Science (EMS)™, Hatfield, Pa.) then fixed in a solution of 2.5% gluteraldehyde-formaldehyde in 0.1 M sodium cacodylate buffer (#15949, Electron Microscopy Science (EMS)™, Hatfield, Pa.), 0.3 M sucrose (Sigma®, St. Louis, Mo.), 1% DMSO (Sigma®, St. Louis, Mo.) pH 7.4 overnight at 4° C. The fixed tissue was washed three times in 0.1M sodium cacodylate buffer, pH 7.4 buffer, post-fixed stained in 0.1 M tannic acid (#21700, Electron Microscopy Science (EMS)™, Hatfield, Pa.) in 0.1 M sodium cacodylate pH 7.4 for 3 hours at room temperature. The tissue samples were washed three times in buffer, and then fixed again in 1.0 M osmium tetroxide (#19152, Electron Microscopy Science (EMS)™, Hatfield, Pa.) in cacodylate buffer pH 7.4 for 1.5 hours at room temperature. Samples were dehydrated in a series of graded ETOH, and then embedded in EMBED-812™ resin (#14120, Electron Microscopy Science (EMS)™, Hatfield, Pa.). Samples were sectioned at yellow-silver (700 A), mounted on Ni grids and examined under a JEOL-JEM 1010™ transmission electron microscope (JEOL®, Peabody, Mass.) at 80 kV.

Scanning Electron Microscopy (SEM)

Samples from the RWV cultures were taken for SEM at the same times as those taken for growth kinetics and immunocytochemistry. After removal from the reactor vessels, samples were washed once with CMF-PBS. The samples were suspended in a buffer containing 3% glutaraldehyde and 2% paraformaldehyde in 0.1 M cacodylate buffer at pH 7.4 (Luna, 1968), then rinsed for 5 minutes with cacodylate buffer three times and post-fixed with 1% osmium tetroxide (Electron Microscopy Science (EMS)™, Hatfield, Pa.) in cacodylate buffer for 1 hour. Samples were then rinsed three times for 5 minutes each with distilled water and then treated for 10 minutes with a Millipore® (Bedford, Mass.) (0.2-μm)-filtered, saturated solution of thiocarbohydrazide (Electron Microscopy Science (EMS)™, Hatfield, Pa.), then washed five times for 5 minutes each with distilled water and fixed with 1% buffered osmium tetroxide for 10 minutes. This last step was necessary to prevent the microcarriers from collapsing. Samples were then rinsed with distilled water three times and dehydrated with increasing concentrations of EtOH, followed by three changes in absolute methanol. After transfer to 1,1,1,3,3,3-hexamethyldisilazane (Electron Microscopy Science (EMS)™, Hatfield, Pa.), samples were allowed to soak for 10 minutes, drained, and air-dried overnight. Dried samples were sprinkled with a thin layer of silver paint on a specimen stub, dried, coated by vacuum evaporation with platinum-palladium alloy, and then examined in the JEOL T330™ scanning electron microscope (JEOL®, Peabody, Mass.) at an accelerating voltage of 5 to 10 kV.

Viral Infection of TLAs

TLAs were infected as described previously. Briefly, TLAs were inoculated with wtRSV A2 (Lewis et al, 1961) and wtPIV3 JS (Belshe et al, 1982) at a MOI of 0.1. After virus absorption at room temperature for one hour, monolayers and TLA cultures were washed 3 times with DPBS (Invitrogen®, Carlsbad, Calif.) and fed with media specified above. All air bubbles were removed from the RWV before rotation to eliminate shearing of the cells (Goodwin et al, 1988) and before placing in a humidified incubator with 5% $CO_2$ at 35° C. Approximately 65% of the culture media was replaced every 48 hours for both monolayer and TLA cultures. Samples were collected at days 0, 2, 4, 6, 8, and 10 for virus titration. For RSV titration, 1 mL samples of the TLA cultures were flash-frozen with 1×SPG. The titer was determined by immunostaining in HEp-2 cells at 32° C. as previously described (Randolph et al, 1994). Titers of PIV3 viruses were determined in LLC-MK2 cells with medium overlay containing 0.8% agar at 32° C. as previously described (Karron et al, 1995), except that plaques were visualized by an immunostain assay described previously (Randolph et al, 1994) using anti-human PIV3 HN and F antibodies.

Immunostaining Fixed RSV-Infected TLAs

Uninfected and TLAs ($10^6$ cells) infected with wtRSV A2 were fixed at different times post infection (pi) as described (Cheutin et al, 2003). Briefly, EM grade paraformaldehyde (#1570, Electron Microscopy Science (EMS)™, Hatfield, Pa.) was added to a final concentration of 4% after the TLAs were washed three times in DPBS (#21-030-CV, Cellgro®). After one hour, the TLAs were washed 3 more times with DPBS. The TLAs were permeablized in Triton™ X-100 (#T9284, Sigma®, St. Louis, Mo.) for 5 minutes on ice. To avoid nonspecific binding the samples were incubated with 1% BSA for 5 minutes followed by cold water fish gelatin (Fluka #48717) in PBS at room temperature for 10 minutes. The TLAs were incubated with 0.02 M glycine (Fluka Biochemical® #1050586) for 3 minutes to reduce autofluoresence. A 1:1000 dilution of RSV F (133-1H and 143-6C) and G (131-1G) monoclonal antibodies (Anderson et al, 1988) were incubated for one hour; then the TLAs were washed 5 times with 1% BSA. Texas Red dye conjugated AffiniPure™ Goat anti-mouse IgG H+L (Jackson ImmunoResearch Laboratories® #115-075-146) was diluted 1:100 and 500 μL was added to each sample for 1 hour, then washed 4 times with DPBS. TLAs were observed with an Olympus® IX70 fluorescent microscope.

Example 2

Growth Kinetics of TLAs

Figure 3:
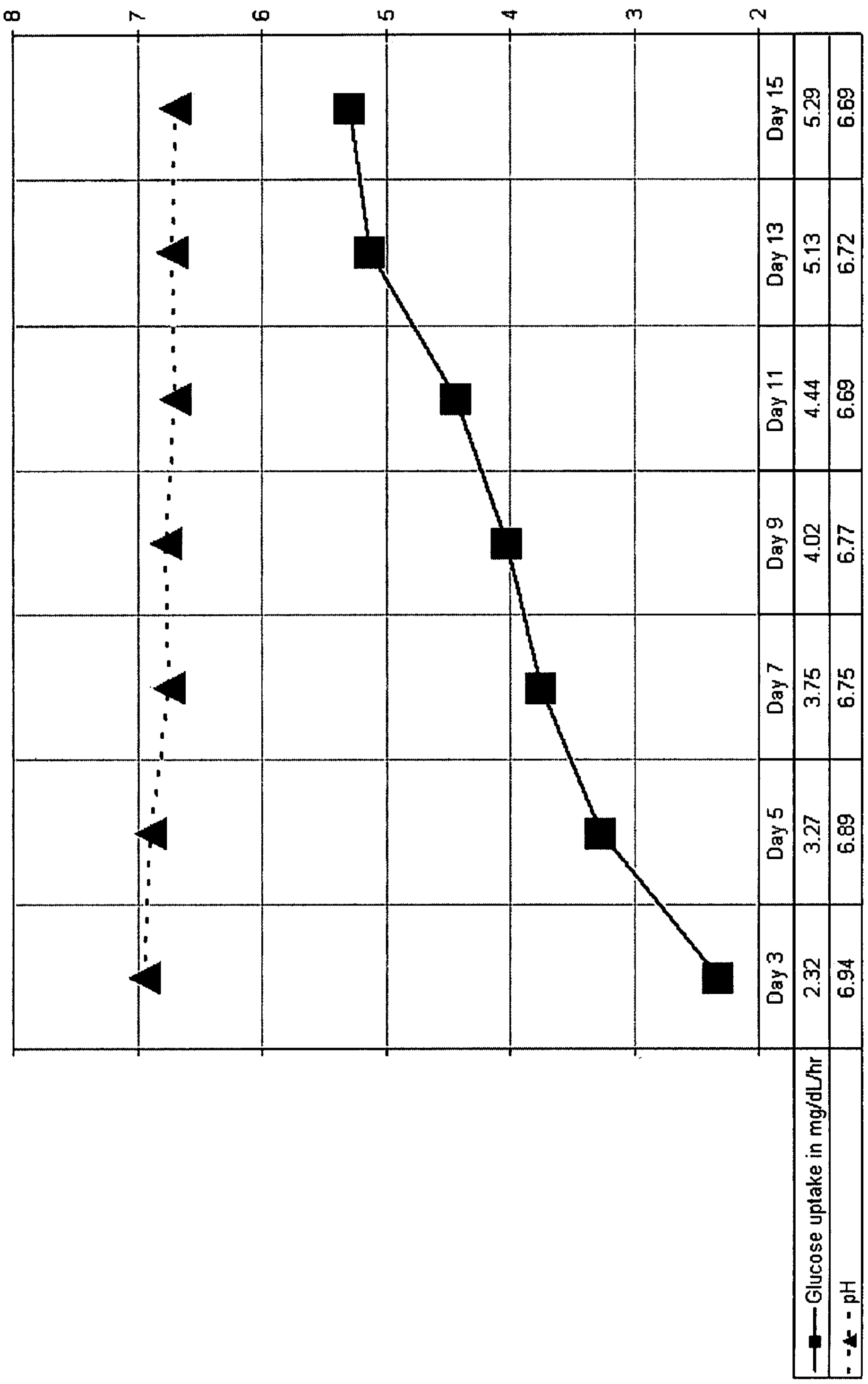
FIG. 3: Glucose utilization. Glucose utilization and pH curves for a healthy 3D culture. Standard error of the Mean for the pH data is <0.08.

TLAs were produced by inoculating a RWV using GTSF-2 media with mesenchymal and epithelial lung cells in the presence of microcarriers. In one embodiment an aliquot of lung cells is expanded using 2D tissue culture flasks, trypsinized to dislodge the cells from the conical tube, bring the cells to a known cell density in an RWV with GTSF-2 media, and incubated under microgravity conditions allowing the formation of TLAs. The cultures were monitored at 24-hour time points for glucose utilization and pH. FIG. 3 reflects a typical metabolic profile for these cultures. These data clearly demonstrate rapid uptake of glucose by TLAs with a slight decrease in pH over the initial growth period. Together these factors indicate an increase in cellular metabolism commensurate with an increase in the size of the aggregates.

In one example, hBTC and BEAS-2B cells were initiated as monolayers in human fibronectin coated flasks and propagated in GTSF-2 media supplemented with 10% fetal bovine serum (FBS). The cells were passaged as required by enzymatic dissociation with a solution of 0.1% trypsin and 0.1% EDTA for 15 minutes at 37° C. The primary inoculum for each 55-ml RWV with 5 mg/ml of Cytodex-3™ microcarriers was $2\times10^5$ hBTC cells/ml. Cultures were allowed to grow for approximately 4 days as previously described. BEAS-2B epithelial cells were added at $2\times10^5$ cells/ml on day 4. As metabolic requirements increased, fresh medium was supplemented with an additional 100 mg/dl of glucose. Experiments were cultured for up to 40 days total. Viable cocultures grown in the RWV were harvested over periods up to 21 days and prepared for various activity assays.

Example 3

TLAs Express Markers of In Vivo Respiratory Epithelium (IHC)

Figure 4:
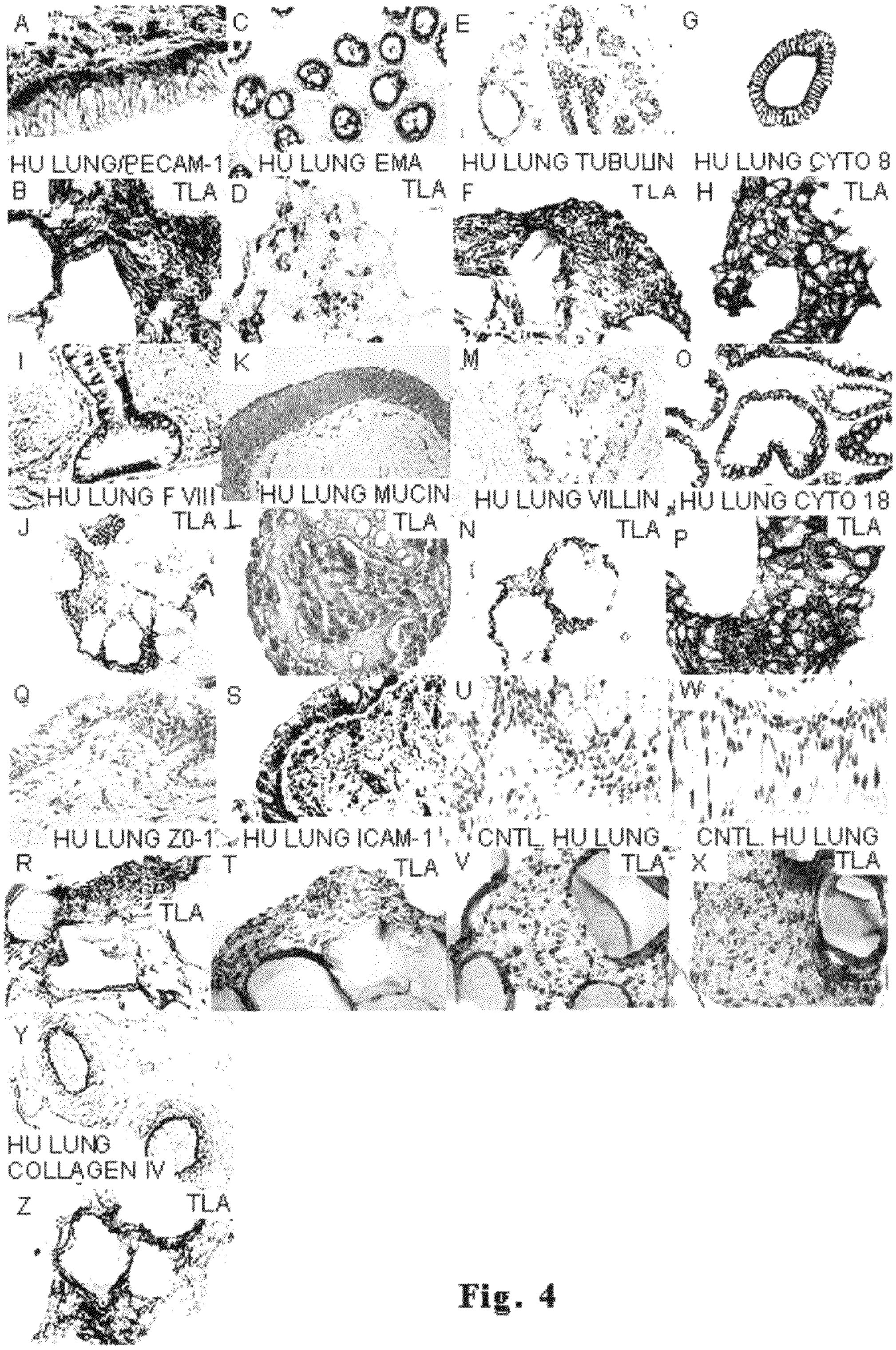
FIG. 4: Comparative IHC staining. Comparative IHC staining of normal human lung tissue samples (FIG. 4A, FIG. 4C, FIG. 4E, FIG. 4G, FIG. 4I, FIG. 4K, FIG. 4M, FIG. 4O, FIG. 4Q, FIG. 4S, FIG. 4U.

To compare the cellular composition and differentiation state of TLAs to normal human respiratory epithelium, fixed TLAs and normal human lung sections were immunostained for epithelial specific cell markers (FIG. 4, Table 4). The cytokeratins (Ke, 1988; Sutherland, 1988) (FIG. 4G, FIG. 4H, FIG. 4O, FIG. 4P) and Factor VIII (FIG. 4I, FIG. 4J) antibodies detect epithelial, mesenchymal, and endothelial cells, respectively (Tsao, et al, 1992, Moyer, 1990, Woodcock-Mitchell, et al, 1982, Vogel, et al, 1984, Shima, et al 1988). Tubulin (FIG. 4E, FIG. 4F), is a cytoskeletal protein found in epithelial cells. Endothelial markers, PECAM-1 (FIG. 4A, FIG. 4B) and Factor VIII (FIG. 4I, FIG. 4J), are present in subsets of precursor endothelial cells, particularly dividing cells. Basement membrane and extracellular matrix components (e.g., collagen IV; FIG. 4Y, FIG. 4Z) were also assayed to determine their expression in the TLAs. Expression of endothelial specific and basement membrane components (FIG. 4J, FIG. 4Z) were frequently seen at cell-bead-aggregate interfaces. Other markers were also selected to highlight epithelial characteristics including microvilli (Villin; FIG. 4M, FIG. 4N) tight junctions (ZO-1; FIG. 4Q, FIG. 4R), and polarization (EMA; FIG. 4C, FIG. 4D). Expression of ICAM-1 (FIG. 4S, FIG. 4T) and cytokeratin 18 (FIG. 4O, FIG. 4P) reflect a differentiated state. Positive staining for mucin (FIG. 4K, FIG. 4L) indicates production of mucus in the tissue. Of particular interest, FIG. 4T, FIG. 4N, and FIG. 4F illustrate homogenous staining for cytoskeletal markers, ICAM-1, villin, and tubulin at the surfaces of most areas of the cell/microcarrier TLAs. Each of the cell specific cellular stains applied to TLAs compared favorably with the 3D human tissue controls shown in Table 5, thus confirming that fidelity to in situ respiratory epithelia is achieved.

TABLE 5

NATIVE CELLULAR DIFFERENTIATION

| Tissue Characterization Stains | 3D/Nor Hu Lung Tissue | 3D/TLA/BEAS-2B/ |
|---|---|---|
| ICAM-1 | 4+ | 3+ |
| Villin | 2+ | 3+ |
| Tubulin | 3+ | 4+ |
| Cytokeratin 8 | 4+ | 3+ |
| Cytokeratin 18 | 3+ | 4+ |
| PECAM-1 | 3+ | 4+ |
| ZO-1 | 2+ | 3+ |
| EMA | 4+ | 2+ |
| Hu Mucin | 4+ | 4+ |
| VWR/Factor VIII | 4+ | 3+ |
| Collagen IV | 4+ | 4+ |

Slides were scored on a relative scale: 0 (no staining), 1+ (weak staining), 2+ weak staining for 25-50% of the cells, 3+ indicates moderate staining for 50-75% of the cells, and 4+ indicates staining of 99% of the cells.

Example 4

TLAs Display Structural Characteristics of the Human Respiratory Epithelia

Figure 5:
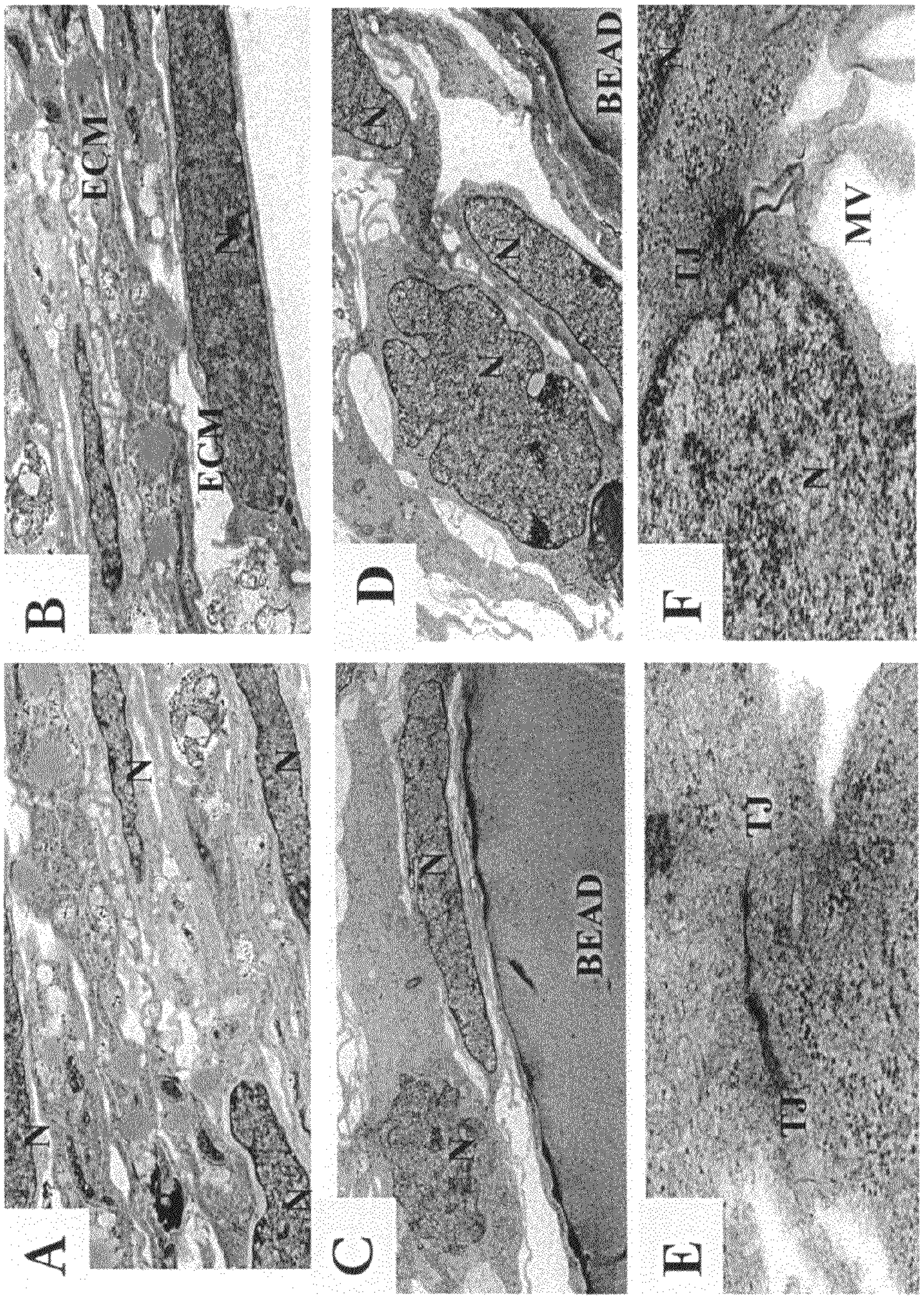
FIG. 5: TEMs of uninfected TLAs.

TEMs of uninfected TLAs (FIG. 5A-FIG. 5F) illustrate many features of normal tissue and demonstrate recapitulated respiratory epithelium polarized with apical and basolateral sides reinforcing the IHC data. TEMs of thin sections of TLAs illustrate human respiratory epithelial characteristics including a multi-layered structure punctuated by extracellular matrix and pseudo-stratified mesenchymal and epithelial layers (FIG. 5A, FIG. 5B). Multiple cell types are shown in (FIG. 5C, FIG. 5D); the nuclei of mesenchymal cells (on bead) are elongated and the nuclei of epithelial cells are rounded. FIG. 5E and FIG. 5F the center of both micrographs demonstrates conformational data showing tight junctions (TJ) also represented by ZO-1 IHC staining. Microvilli, stained by villin and tubulin on IHC can be seen in FIG. 5F. In light of the functional studies above and these structural studies, the recapitulated 3D models emulate complex cellular relationships of in situ airway epithelium.

Example 5

TLAs Infection with Respiratory Viruses

TLAs produced as described in Example 1, were infected with wtRSV A2 and wtPIV3 JS. In one embodiment, TLAs were inoculated with wtRSV A2 and wtPIV3 JS at a MOI of 0.1. After virus absorption at room temperature for one hour, monolayers and TLA cultures were washed 3 times with DPBS and fed with media specified above. All air bubbles were removed from before placing in a humidified incubator. Media was replaced every 48 hours. Samples were collected at days 0, 2, 4, 6, 8, and 10 for virus titration. Similar 2D cultures were treated similarly as a control.

Scanning Electron Microscopy (SEM)

Figure 6:
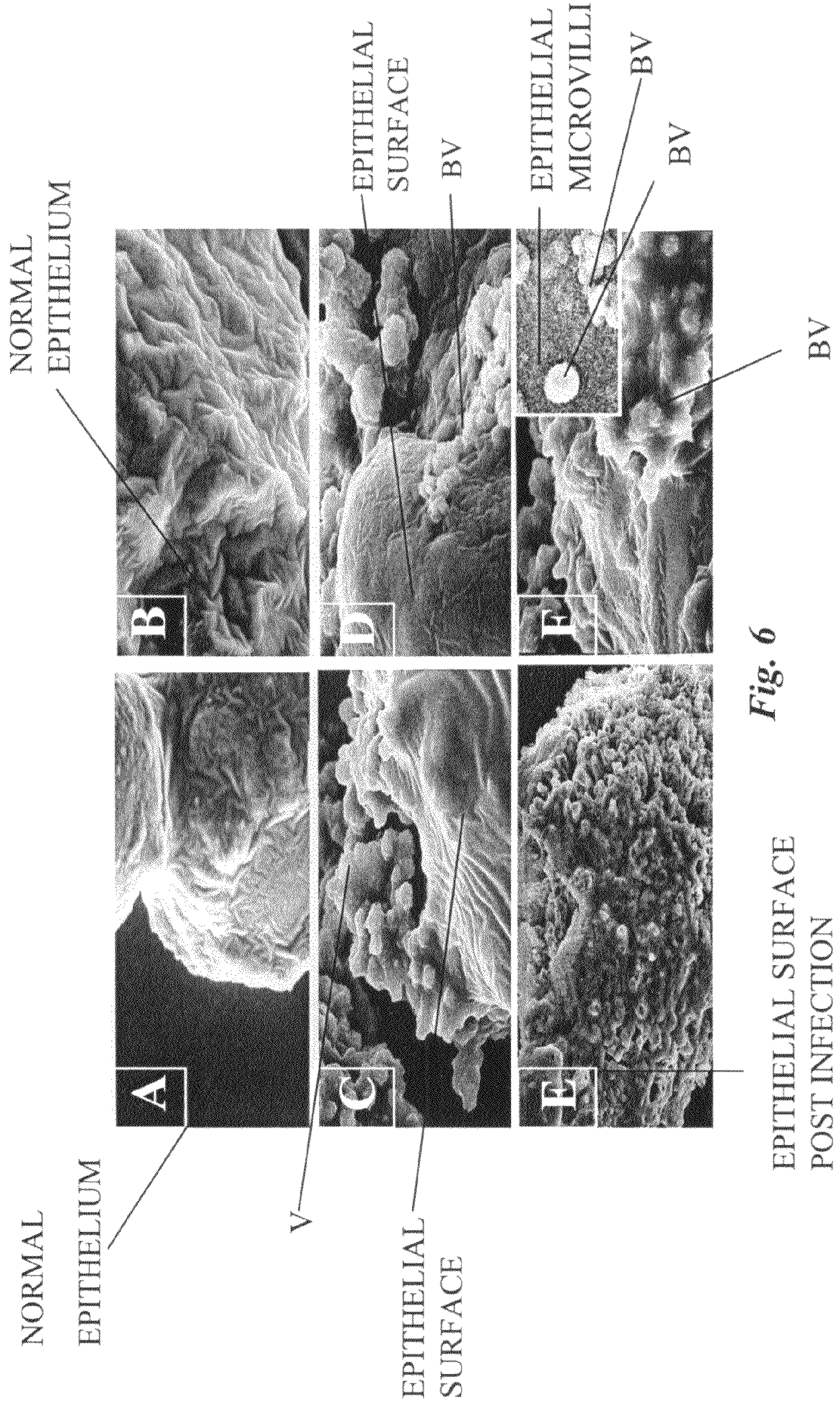
FIG. 6: SEMs of TLAs infected with wtRSVA2.

TLA samples were collected at intervals across the initial growth experiment (FIG. 6A, FIG. 6B uninfected) and post infection (pi) (FIG. 6C-FIG. 6F) and were prepared for scanning electron microscopy as stated previously. Photomicrographs taken of day 2-12 cocultures pi showed viral presence and cellular damage (FIG. 6C, FIG. 6D). FIG. 6E demonstrates cell surface damage analogous to pockmarks at 8 days pi. In FIG. 6F, 12 days pi, an insert of budding virus is visible. Samples harvested at approximately 12 days of culture contained small microcarrier bead packs that were totally engulfed in proliferating TLA epithelium despite viral infection (FIG. 6E, FIG. 6F). Additionally, at 21 days large proliferating masses of TLAs (>3.5 mm) were evident, growing on the microcarrier bead packs pi.

Transmission Electron Microscopy (TEM)

Figure 7:
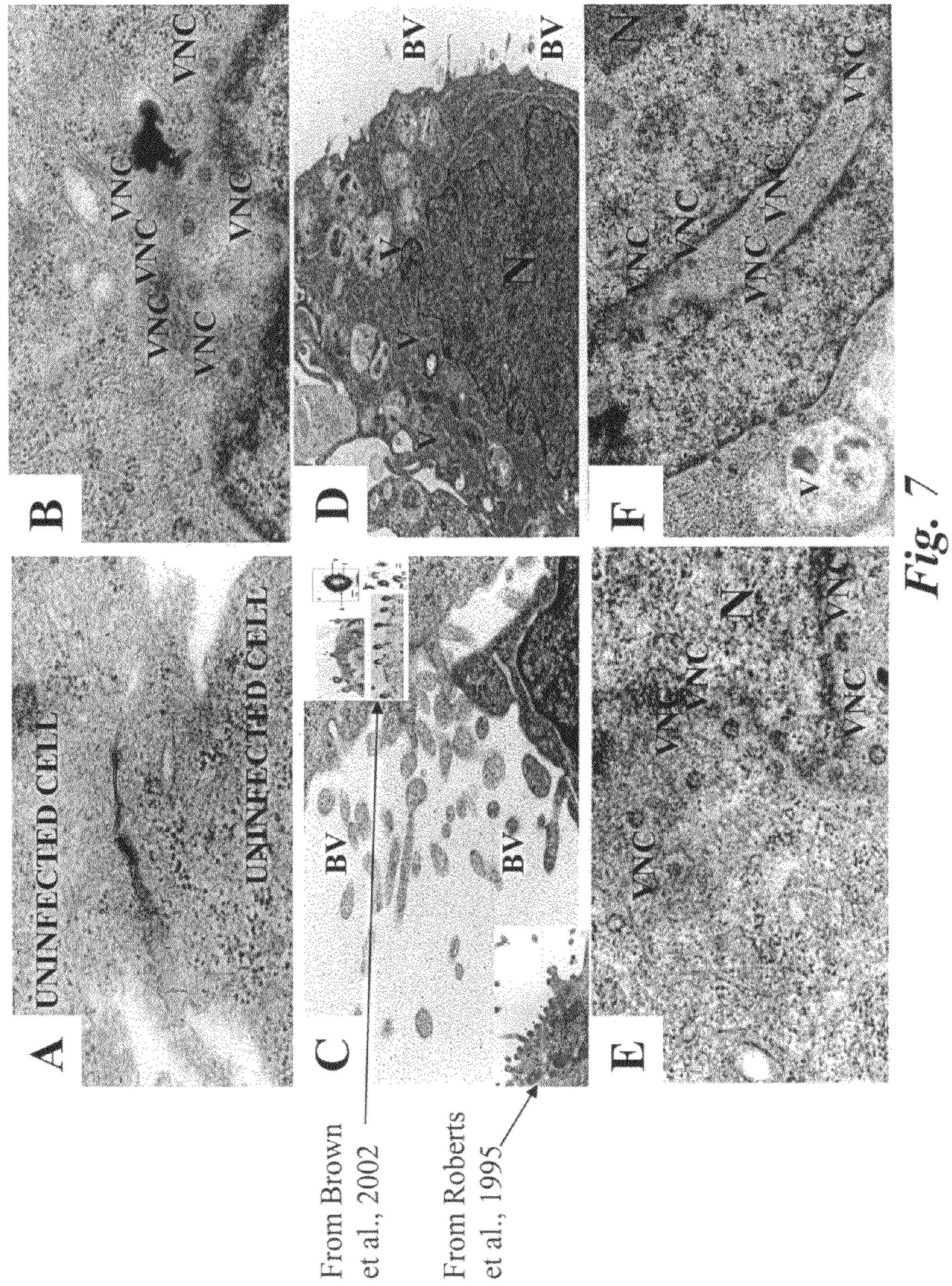
FIG. 7: TEMs of wtRSVA2 infected TLA epithelium.
Figure 8:
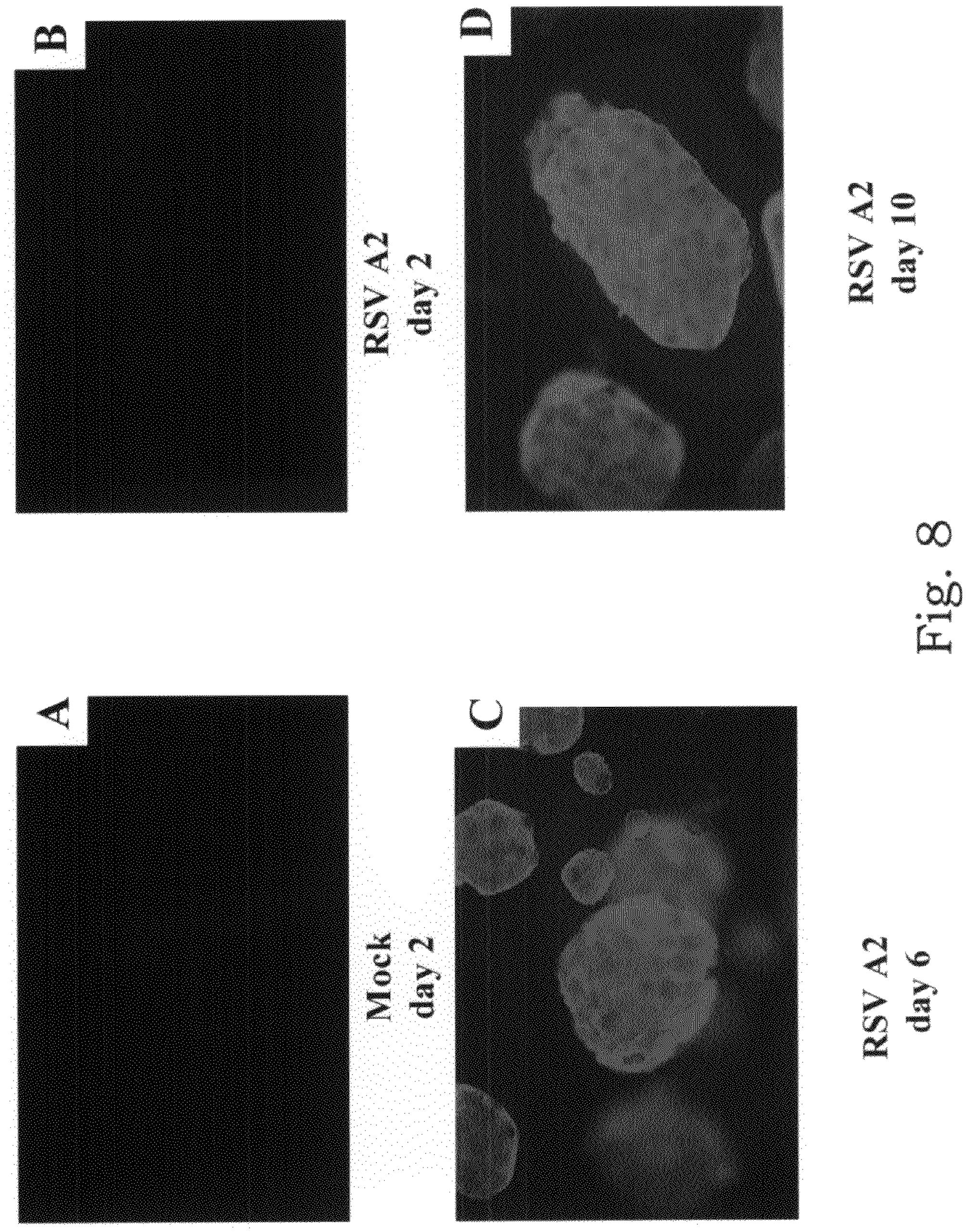
FIG. 8: Expression of RSV. Increase in expression of RSV FIG. 8F and FIG. 8G glycoproteins from day 2 to 10 pi.

TLAs were infected as previously stated. (FIG. 7A-FIG. 7F) illustrates the time course of infection into the TLAs from 0-12 days respectively. TEMs of all TLAs subjected to virus demonstrated infection beginning as early as 1 hour pi, FIG. 7B, and continuing through day 12 pi FIG. 7F. Viral nucleocapsids (VNC) were found to locate through out the cells and in the perinuclear regions (FIG. 7B, FIG. 7E and FIG. 7F) and were overtly apparent in both RSV and PIV3 infected TLAs. Mature virus particles are formed when VNCs bud from the cell membrane containing the viral glycoproteins thus budding virus was present beginning at day 2 (FIG. 7C) and day 4 (FIG. 7D) and continuing throughout the course of the infection.

Viral Protein and Titer Data

Figure 9:
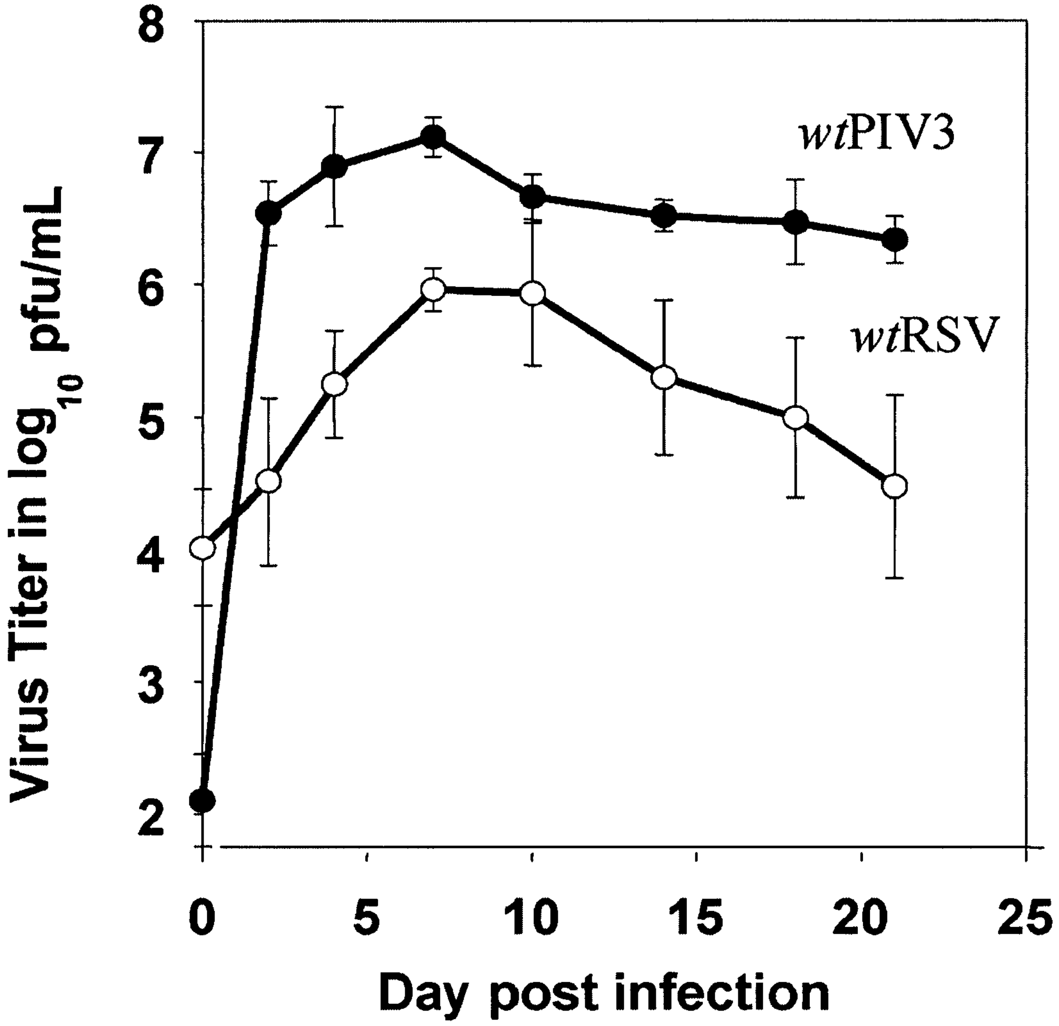
FIG. 9: Growth kinetics. Growth kinetics of wtRSVA2 and wtPIV3 JS in recapitulated TLAs up to day 21.

Photographs of fluorescently stained TLAs, specific for two RSV glycoproteins (F and G) that increased in concentration (Days 2-10), are shown in (FIG. 8A-FIG. 8D). FIG. 9 illustrates viral growth kinetics up to day 21 pi with wtRSVA2 and wtPIV3 JS. As illustrated, wtPIV3 JS replicates more efficiently than wtRSVA2 in TLAs. Peak replication is on day 7 for wtPIV3 JS (approximately 7 log 10 particle forming units (pfu) per mL) and on day 10 for wtRSVA2 (approximately 6 log 10 pfu/mL).

TLAs provide an exemplary model of human lung tissue, forming 3D tissue models of in situ respiratory epithelial cells. The infection of these cells with RSV and PIV is one indication of complex respiratory epithelia formation. The budding virus particles, progression of infection and long term growth of the infected TLAs provide a background for additional assays and monitoring of disease progression in vitro.

Example 6

Screening for Antiviral Compounds (Prophetic)

TLAs produced as described in the above examples and infected with a virus as previously described, provide an in vitro model for lung infection. To identify antiviral compounds TLAs infected with a virus provide a method of screening libraries of compounds for antiviral activity and lung tissue toxicity. TLAs contacted with a test compound are compared to TLAs contacted with a known compound, TLAs infected with a virus only, and uninfected TLAs only. Antiviral activity can be measured phenotypically by noting viral bud formation or quantitatively by counting the number and size of virus buds. Other measures of cellular or viral activity are known and can be easily measured.

In one embodiment, TLAs are produced and infected with a viral strain. Infected and non-infected TLAs are placed in a series of cultures (from arrayed slides or microplates to larger cultures or RWV) and growth is compared in the presence or absence of antiviral compounds. Various measures of viral titer and TLA viability can then be assessed in vitro including the methods described in the previous examples. Antiviral compounds such as zinc, TAMIFLU™ (oseltamivir phosphate), WIN 52084 (anti-rhinoviral) or other antivirals can be compared to test compounds in a laboratory setting using the TLA model system.

Example 7

Screening for Cystic Fibrosis Treatments (Prophetic)

TLAs produced as described in Example 1, can be created using cystic fibrosis (CF) variants of HBEs including CFSMEo, CFBE41o-, and IB3-1. By comparing the surfactants, proteases, and mucous produced with CF epithelium to normal HBEs, differences in the TLAs can be measured qualitatively and quantitatively. To identify novel CF treatments, CF-TLAs can be used to screen libraries of compounds for changes in mucous, increase in surfactant, and other properties of normal or CF epithelia. Similar TLAs with known CF treatments and without a test compound provide positive and negative controls. CF-TLAs can also be assayed along with WT TLAs to provide additional controls.

In one embodiment, TLAs are produced with hBTC mesenchymal cells and either CFSMEo (CF) or BEAS-2B (wt) epithelial cells as previously described. Cultures of CF TLAs and wt TLAs are isolated and split into 2 sets of cultures. One pair of CF and wt cells are exposed to a test compound (experimental), the other pair are similarly treated in the absence of test compound (control). Cell morphology, mucous, and surfactant measurements are made. Candidate compounds that reduce CF related traits in TLAs can be identified and used to develop CF treatments.

Example 8

Assessing Allergens and Lung Toxicity (Prophetic)

TLAs provide an in vitro model of lung tissue. They produce inflammatory response modifiers, endocrine, autocrine, paracrine, and cytokine factors that are indicative of allergic response. Similar TLAs exposed to known allergens, irritants, and/or unknown test compounds provide a rapid in vitro assay of allergens and/or lung tissue toxicity.

In one embodiment, TLAs are produced with hBTC mesenchymal cells and BEAS-2B epithelial cells as previously described. Cultures TLAs are isolated and spread onto a matrix of known (control) and test compounds (experimental). Cell markers, including apoptosis markers and inflammatory response modifiers, are used qualitatively or quantitatively measure the effect of known and test compounds over time. Compounds which reduce or delay the onset of inflammatory response are identified as anti-allergenic compounds. Compounds which induce apoptotic response are identified as cytotoxic.

REFERENCES

All references are listed herein for the convenience of the reader. Each is incorporated by reference in its entirety.

1. U.S. Pat. No. 4,885,238 Reddel, et al., "Immortalized Human Bronchial Epitherial Mesothelial Cell Lines." (1989).
2. U.S. Pat. No. 4,988,623 Schwartz, et al., "Rotating Bioreactor Cell Culture Apparatus." (1991).
3. U.S. Pat. No. 5,026,650 Schwarz, et al., "Rotating cell culture vessel." (1991).
4. U.S. Pat. No. 5,153,132 Goodwin, et al., "Three-Dimensional Co-culture Process." (1992)
5. U.S. Pat. No. 5,153,133 Schwarz, et al., "Method for Culturing Mammalian Cells in a Horizontally Rotated Bioreactor." (1992)
6. U.S. Pat. No. 5,155,034 Wolf, et al., "Three-Dimensional Cell to Tissue Assembly Process." (1992)
7. U.S. Pat. No. 5,155,035 Schwarz, et al., "Method for Culturing Mammalian Cells in a Perfused Reactor." (1992).
8. U.S. Pat. No. 5,308,764 Goodwin et al., "Multi-Cellular, Three-Dimensional Living Mammalian Tissue." (1994).
9. U.S. Pat. No. 5,496,722 Goodwin et al., "Method for Producing Non-Neoplastiac, Three-Dimensional, Mammalian Tissue and Cell Aggregates Under Microgravity Culture Conditions and the Products Produced Therefrom." (1996).
10. U.S. Pat. No. 5,627,021 Goodwin et al., "Muti-Cellular, Three-Dimensional Living Mammalian Tissue." (1997).
11. U.S. Pat. No. 5,443,954 Reddel, et al., "Immortalized Non-Tumorigenic Human Bronchial Epithelial Cell Lines." (1995).
12. U.S. Pat. No. 5,478,739 Slivka, et al., "Three-Dimential Stromal Cell and Tissue Culture System." (1995)
13. U.S. Pat. No. 5,516,680 Naughton, et al., "Three-Dimensional Kidney Cell and Tissue Culture System." (1996)
14. U.S. Pat. No. 5,846,807 Goodwin, "Media compositions for three-dimensional mammalian tissue growth under microgravity culture conditions." (1998).
15. U.S. Pat. No. 5,962,324 O'Connor, et al., "Three Dimensional Optic Tissue Culture and Process." (1999).
16. U.S. Pat. No. 6,117,674 Goodwin, et al., "Pathogen Propagation in Cultured Three-Dimensional Tissue Masses." (2000).

17. U.S. Pat. No. 6,133,019 Herman, "Centrifugal Fermentation Process." (2000).

18. U.S. Pat. No. 6,607,910 Dimitrijevich, et al., "Two Chamber Cell Culture Vessel." (2003).

19. U.S. Pat. No. 6,703,217 Herman, et al., "Methods and Devices for Remediation and Fermentation." (2003).

20. US2003/0054546 Petrecca, et al., "Biocatalyst Chamber Encapsulation System for Bioremediation and Fermentation." (2003)

21. US2004/0023374 Rappaport, et al., "Method and Apparatus for Multi-Layer Growth of Anchorage Dependent Cells." (2004)

22. US2004/0175707 Hammond, et al., "Methods for Modeling Infections Disease and Chemosensitivity in Cultured Cells and Tissues." (2004)

23. US2005/0255583 DePaola, et al., "Diamagnetic Force Field Bioreactor." (2005)

24. US2006/0054546 Ma, "Neural Stem Cell-Collagen-Bioreactor System to Construct a Functional Embryonic Brain-like Tissue." (2006)

25. WO00/54583 Kil, et al., "Methods for Culturing Fluid-Filled Sensory Organs." (2000)

26. WO2005/056072 Kida, et al., "Method of Constructing Three-Dimensional Cartilage Tissue By Using Myeloid Cells in Pseudo Microgravity Environment." (2000)

27. Adler and Li, "*Airway epithelium and mucus. Intracellular signaling pathways for gene expression and secretion*." Am. J. Respir. Cell. Mol. Biol. 25:397-400 (2001).

28. Anderson, et al., "*Neutralization of respiratory syncytial virus by individual and mixtures of F and G protein monoclonal antibodies*." J. Virol. 62:4232-8 (1988).

29. Baker and Goodwin, "*Three-dimensional culture of bovine chrondrocytes in rotating-wall vessels*." In vitro Cellular & Dev. Biol. 33:358-65, (1997).

30. Bals and Hiemstra, "*Innate immunity in the lung: how epithelial cells fight against respiratory pathogens*." Eur. Respir. J. 23:327-33 (2004).

31. Belshe and Hissom, "*Cold adaptation of parainfluenza virus type* 3*: induction of three phenotypic markers*." J. Med. Virol. 10:235-42 (1982).

32. Blay and Brown, "*Functional receptors for epidermal growth factor in an epithelial-cell line derived from the rat HBTC/BEAS-*2*B TLA*." Biochem. J. 225:85-94, (1985).

33. Bursac, et al., "*Cultivation in rotating bioreactors promotes maintenance of cardiac myocyte electrophysiology and molecular properties*." Tissue Eng. 9:1243-53 (2003).

34. Carterson, et al., "*A*549 *lung epithelial cells grown as three-dimensional aggregates: Alternative tissue culture model for Pseudomonas aeruginosa pathogenesis*." Infection and Immunity 73:1129-40 (2005).

35. Cheutin, et al., "*Three-dimensional organization of pKi-*67*: A comparative fluorescence and electron tomography study using fluoronanogold*." J. Histochemistry & Cytochemistry 51:1411-23, (2003).

36. Cotran, et al., Robbins Infectious Diseases, Edn. 6$^{th}$ p. 347 (WB Saunders Company, Philadelphia; 1999).

37. Garofola and Haeberle, "*Epithelial regulation of innate immunity to respiratory syncytial virus*." Am. J. Respir. Cell Mol. Biol. 23:581-85 (2000).

38. Gibson and Perrimon, "*Apicobasal polarization: epithelial form and function*." Curr. Opin. Cell Biol. 15:747-52 (2003).

39. Goodwin, "*Physiological and Molecular Genetic Effects of Time-Varying Electromagnetic Fields on Human Neuronal Cells*," NASA Technical Paper-2003-212054 (2003).

40. Goodwin, et al., "*In vitro Three Dimensional Modeling. Annual report of Johnson Space Center Research and Technology*." Pp156-157 (1988).

41. Goodwin, et al., "*Morphologic differentiation of colon carcinoma cell lines HT-*29 *and HT-*29*KM in rotating wall vessels*." In vitro Cell. Dev. Biol. 28A:47-60 (1992).

42. Goodwin, et al., "*Physiological And Molecular Genetic Effects Of Time Varying Electromagnetic Fields* (*TVEMF*) *On Human Neuronal Cells*." Med. Sci. Sports Exercise, Vol. 37:5 Suppl. (2005).

43. Goodwin, et al., "*Reduced shear stress: a major component in the ability of mammalian tissues to form three-dimensional assemblies in simulated microgravity*." J. Cell Biochem. 51:301-11 (1993).

44. Goodwin, et al., "*Rotating-wall vessel coculture of small intestine as a prelude to tissue modeling: aspects of simulated microgravity*." Proc. Soc. Exp. Biol. Med. 202:181-92 (1993).

45. Goodwin, et al., "*Three-dimensional culture of a mixed mullerian tumor of the ovary: expression of in vivo characteristics*." In vitro Cell. Dev. Biol. 33:366-74 (1997).

46. Gray, et al., "*Mucociliary differentiation of serially passaged normal human tracheobronchial epithelial cells*." Am. J. Respir. Cell Mol. Biol. 14:104-12 (1996).

47. Hammond, et al., "*Gene Expression in Space." Nat. Med.* 5:359 (1999).

48. Hiemstra and Bals, "*Series Introduction: innate host defense of the respiratory epithelium*." J. Leukocyte Biol. 75:3-4 (2004).

49. Karron, et al., "*A live human parainfluenza type* 3 *virus vaccine is attenuated and immunogenic in healthy infants and children*." J. Infect. Dis. 172:1445-50 (1995).

50. Ke, et al., "*Human bronchial epithelial cells with integrated SV*40 *virus T antigen genes retain the ability to undergo squamous differentiation*." Differentiation 38:60-6 (1988).

51. Klement, et al., "*Skeletal Tissue Growth, Differentiation, and Mineralization in the NASA Rotating Wall Vessel*." Bone 34:487-98 (2004).

52. Knight and Holgate, "*The airway epithelium: structural and functional properties in health and disease*." Respirology 8:432-46 (2003).

53. Lewis et al., "*A syncytial virus associated with epidemic disease of the lower respiratory tract in infants and young children*." Med. J. Aust. 2:932-3 (1961).

54. Luna, (Ed.), "*Histologic staining methods*." In: American Registry of Pathology, 3$^{rd}$ ed. New York: Armed Forces Institute of Pathology, (1968).

55. Margolis, et al., "*Lymphocyte trafficking and HIV infection of human lymphoid tissue in a rotating wall vessel bioreactor*." AIDS Res. and Human Retroviruses. 13:1411-20 (1997).

56. McFadden, et al., "*Thermal mapping of the airways in humans*." J. Appl. Physiol. 58:564-70 (1985).

57. Moyer, "*Mechanisms of tumor initiation and progression*." Perspect. Gen. Surg. 1:71-91 (1990).

58. Moyer, "*Methods for propagation and characterization of human GI and other cells for study of HIV*." J. Tiss. Cult. Meth. 13:107-16 (1991).

59. Moyer, et al., "*Infection of human gastrointestinal cells by HIV-*1." AIDS Res. Hum. Retroviruses 6:1409-15 (1990).

60. Moyer, et al., "*The in vitro propagation and characterization of normal, preneoplastic and neoplastic colonic epithelial cells*." In: Moyer and Poste (Eds.), Colon Cancer Cells. San Diego: Academic Press, pp 85-136 (1990).

61. O'Brien, et al., "*Building epithelial structure: insights from three-dimensional culture models*." Nature Reviews 3:531-7 (2002).

62. Pellis, et al., "*Changes in Gravity Inhibit Lymphocyte Locomotion through Type I Collagen*." In vitro Cell Dev. Biol. Anim. 33:398-405 (1997).

63. Polito and Proud, "*Epithelial cells as regulators of airway inflammation*." J. Allergy Clin. Immunol. 102:714-8 (1998).

64. Quaroni, "*Crypt cell development in newborn rat HBTC/ BEAS-2B TLA*." J. Cell Biol. 100:1601-10 (1985).

65. Randolph, et al., "*Attenuated temperature-sensitive respiratory syncytial virus mutants generated by cold adaptation*." Virus Res. 33:241-59 (1994).

66. Schwarz, et al., "*Cell culture for three dimensional modeling in rotating-wall vessels: An application of simulated microgravity*." J. Tiss. Cult. Meth. 14:51-8 (1992).

67. Shima, et al., "Factor VIII polypeptide specificity of monoclonal anti-factor VIII antibodies. Br. J. Haematol. 70, 63-69 (1988).

68. Stoner, et al., "*Identification and culture of human bronchial epithelial cells*." Methods Cell. Biol. 21A:15-35 (1980).

69. Sutherland, "*Cell and environment interactions in tumor microregions: The multicell spheroid model*." Science 240: 177-84 (1988).

70. Tsao, et al., "*Responses of gravity level variations on the NASA/JSC bioreactor system*." The Physiologist 35:549-50 (1992).

71. Vertrees, et al., "*Synergistic interaction of hyperthermia and gemcitabine in lung cancer*." Cancer Biol. Ther. 4: 1144-53 (2005).

72. Visage, et al., "Coculture of mesenchymal stem cells and respiratory epithelial cells to engineer a human composite respiratory mucosa." Tissue Engineer. 10: 1426-35 (2004).

73. Vogel and Gown, "*Monoclonal antibodies to intermediate filament proteins*." In: Shay (Ed.) Cell and Muscle Motility. New York: Plenum Publishing, Vol 5: pp 379-402 (1984).

74. Wang, et al., "*Three-dimensional co-culture models to study prostate cancer growth, progression, and metastasis to bone*." Review: Seminars in Cancer Biology 15:353-4 (2005).

75. Whiticutt, et al., "*A biphasic chamber system for maintaining polarity of differentiation of cultured respiratory tract epithelial cells*." In vitro Cell. Dev. Biol. 24:420-8 (1988).

76. Woodcock-Mitchell, et al., "*Immunolocalization of keratin polypeptides in human epidermis using monoclonal antibodies*." J. Cell Biol. 95:580-8 (1982).

77. Wright, et al., "*Growth of respiratory syncytial virus in primary epithelial cells from the human respiratory tract*." J. Virology 79:8651-4 (2005).

78. Wu, et al., "*Developing differentiated epithelial cell cultures: airway epithelial cells*." Fundam. Appl. Toxicol. 6:580-90 (1986).

79. Yoffe, et al., "*Cultures of human liver cells in simulated microgravity environment*." Adv. Space Res. 24:829-36 (1999).

What is claimed is:

1. A method of assaying a test compound for a therapeutic, allergenic, or cytotoxic activity with three-dimensional human broncho-epithelial tissue-like assemblies comprising:

inoculating a rotating wall vessel comprising microcarriers in culture media with mesenchymal bronchial-tracheal cells, wherein said microcarriers and said culture media are selected to have a difference in density from 90% to 95% or 105% to 110%, wherein said difference in density is defined as 100 times the fraction of the microcarrier's density over the culture media's density;

growing bronchial-tracheal cells for 24 to 240 hours;

inoculating said rotating wall vessel with bronchial epithelium cells to generate a coculture;

growing said coculture for 24 to 960 hours to produce tissue-like assemblies wherein said tissue-like assemblies express markers of in vivo respiratory epithelia and display structural characteristics of in vivo respiratory epithelia;

dividing said coculture into two or more separate cocultures comprising at least one experimental tissue like assembly and one or more control tissue-like assemblies;

incubating said at least one experimental tissue-like assembly and said one or more control tissue-like assemblies under similar conditions;

infecting said at least one experimental tissue-like assembly with a virus;

proliferating said virus for a predetermined timeframe up to about 504 hours;

contacting at least one experimental tissue-like assembly from a first coculture to said test compound, wherein said test compound is an antiviral compound;

measuring a phenotypic, genetic or quantitative trait for each tissue-like assemblies; and determining said therapeutic, allergenic, or cytotoxic activity of said antiviral compound by comparing said phenotypic or quantitative trait in said at least one experimental tissue-like assembly to said one or more control tissue-like assemblies.

2. The method of claim 1, wherein said virus is selected from the group consisting of respiratory syncytial virus (RSV), human respiratory syncytial virus A-2, human respiratory syncytial virus B, human respiratory syncytial virus 9320, human respiratory syncytial virus Wash/18537/'62, human respiratory syncytial virus Long (VR-26), parainfluenza virus (PIV), parainfluenza virus 1, parainfluenza virus 2, parainfluenza Greer, Parainfluenza 4a, parainfluenza 4b, parainfluenza 5 DA, human rhinoviruses (HRV), coxsackieviruses, echoviruses, severe acute respiratory syndrome (SARS), adenovirus, influenza A and B, hantavirus, cytomegalovirus (CMV), paramyxovirus species (measles), varicella-zoster virus, Epstein-Barr virus, herpes simplex virus, and human immunodeficiency virus (HIV).

3. The method of claim 1, wherein said bronchial epithelium cells are selected from the group consisting of cystic fibrosis (CF) epithelium, CFSMEo-, and CFBE41o-; and said test compound reduces symptoms of CF.

4. The method of claim 1, wherein said first coculture tissue-like assemblies are assessed for endocrine, autocrine, paracrine, and cytokine factors that are indicative of allergic response.

5. The method of claim 1, wherein said first coculture tissue-like assemblies are assessed for endocrine, autocrine, paracrine, and cytokine factors.

6. The method of claim 1, wherein said rotating wall vessel is comprised of a culture chamber rotatable about an approximately horizontal longitudinal axis, means to controllably rotate said culture chamber, means to introduce an oxygen-containing fluid throughout said culture chamber, and means to remove metabolic waste products therefrom.

7. The method of claim 6, wherein said means to controllably rotate said culture chambers is comprised of controlling the rotation of said culture chamber such that the fluid medium has the following properties;

collocation of said culture media with said bronchial-tracheal cells, essentially no relative motion of said culture media with respect to the boundaries of said chamber, freedom for three-dimensional spatial orientation of said tissue-like assemblies formed by said growing of said coculture.

8. The method of claim 1, wherein said predetermined timeframe is greater than 96 hours.

9. The method of claim 1, wherein the step of proliferating is comprised of:

allowing said virus to absorb into said tissue-like assemblies for about one hour at room temperature, wherein room temperature is a temperature from 20° C. to 25° C.;

washing said at least one experimental tissue-like assembly infected with said virus 3 times with Dulbecco's phosphate buffered saline after said step of allowing; and feeding said at least one experimental tissue-like assembly with a culture media after said step of washing.

10. The method of claim 9, wherein the step of proliferating is further comprised of:

removing substantially all air bubbles from said rotating wall vessel after said step of feeding;

placing said rotating wall vessel in a humidifier after said step of removing.

11. The method of claim 10, wherein said humidifier produces and maintains an environment comprised of about 5% carbon dioxide at a temperature of about 35 degrees Celsius.

12. The method of claim 10, wherein the step of proliferating is further comprised of:

replacing about 65 percent of said culture media about every about 48 hours until the end of said timeframe.

13. The method of claim 1, wherein said measuring step is comprised of immunohistochemistry and results thereof, wherein said markers comprise cytokeratin 8 and cytokeratin 18, and wherein said results comprise staining of 99% of the cells of said tissue-like assemblies for said cytokeratin 18, and from 50% to 75% of the cells of said tissue-like assemblies for said cytokeratin 8.

14. The method of claim 13, wherein said results comprise staining of 99% of the cells of said tissue-like assemblies for said cytokeratin 18.

15. The method of claim 13, wherein said markers further comprise Factor VIII and wherein said results further comprise staining from 50% to 75% of the cells of said tissue-like assemblies for Factor VIII.

16. The method of claim 1, wherein said measuring step is comprised of immunohistochemistry and results thereof, wherein said markers comprise tubulin, and wherein said results comprise staining of 99% of the cells of said tissue-like, assemblies for said tubulin.

17. The method of claim 1, wherein said measuring step is comprised of immunohistochemistry and results thereof, wherein said markers comprise PECAM-1 and Factor VIII, and wherein said results comprise staining from 50% to 75% of the cells of said tissue-like assemblies for said Factor VIII and staining of 99% of the cells of said tissue-like assemblies for said PECAM-1.

18. A method of assaying a test compounds for a therapeutic, allergenic, or cytotoxic activity with three-dimensional human broncho-epithelial tissue-like assemblies comprising:

inoculating a rotating wall vessel comprising microcarriers in culture media with mesenchymal bronchial-tracheal cells, wherein said microcarriers and said culture media are selected to a difference in density from 90% to 95% or from 105% to 110%, wherein said difference in density is defined as 100 times the fraction of said microcarrier's density over said culture media's density;

growing bronchial-tracheal cells for 24 to 240 hours;

inoculating said rotating wall vessel with bronchial epithelium cells to generate a coculture;

growing said coculture for 24 to 960 hours to produce tissue-like assemblies wherein said tissue-like assemblies express markers of in vivo respiratory epithelia and display structural characteristics of in vivo respiratory epithelia;

dividing said coculture into two or more separate cocultures comprising at least one experimental tissue-like assembly from a first coculture and one or more control tissue-like assemblies from one or more cocultures;

contacting said at least one experimental tissue-like assembly to said test compound;

incubating said at least one experimental tissue-like assembly and said one or more control tissue-like assemblies under similar conditions;

measuring a phenotypic, genetic or quantitative trait for each tissue-like assemblies, wherein said measuring stop is comprised of immunohistochemistry and results thereof; and determining said therapeutic, allergenic, or cytotoxic activity by comparing said phenotypic or quantitative trait in said at least one experimental tissue-like assembly to said one or more control tissue-like assemblies.

* * * * *